(12) United States Patent
Groothuis et al.

(10) Patent No.: US 10,702,274 B2
(45) Date of Patent: Jul. 7, 2020

(54) METHOD AND SYSTEM FOR CLOSING LEFT ATRIAL APPENDAGE

(71) Applicant: Edwards Lifesciences Corporation, Irvine, CA (US)

(72) Inventors: Adam Groothuis, Swampscott, MA (US); Steven D. Cahalane, Pelham, NH (US)

(73) Assignee: Edwards Lifesciences Corporation, Irvine, CA (US)

( * ) Notice: Subject to any disclaimer, the term of this patent is extended or adjusted under 35 U.S.C. 154(b) by 204 days.

(21) Appl. No.: 15/606,611

(22) Filed: May 26, 2017

(65) Prior Publication Data
US 2017/0340329 A1 Nov. 30, 2017

Related U.S. Application Data

(60) Provisional application No. 62/342,187, filed on May 26, 2016.

(51) Int. Cl.
*A61B 17/12* (2006.01)
*A61B 17/00* (2006.01)
*A61B 17/04* (2006.01)

(52) U.S. Cl.
CPC .......... *A61B 17/12013* (2013.01); *A61B 2017/00243* (2013.01); *A61B 2017/0475* (2013.01)

(58) Field of Classification Search
CPC .......... A61B 17/0057; A61B 17/12013; A61B 17/12022; A61B 17/12031;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

EP 1034753 A1 9/2000
EP 3531975 A1 9/2019
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Ryan J. Severson
(74) *Attorney, Agent, or Firm* — Thomas C. Richardson

(57) ABSTRACT

The present teachings provide methods for resizing, reducing, and closing left atrial appendage. Specifically, a percutaneous trans-septal access is first established from outside the body to a patient's LAA. At least two tissue anchors are then implanted inside the LAA chamber and along the tissue wall. At least one anchor is implanted near the opening of the LAA camber. Both tissue anchors are pulled together so that the wall of the LAA chamber collapse. The LAA chamber is therefore resized, reduced, and/or closed off completely. This closure method and system could be used alone in closing LAA chamber. This closure method and system could also be used in addition to other treatment mechanisms, such as filling the LAA chamber with space-filling material, then closing off its opening.

17 Claims, 13 Drawing Sheets

(58) Field of Classification Search
CPC ........ A61B 17/12122; A61B 17/12163; A61B 2017/00243; A61B 2017/00623; A61B 2017/00632; A61B 2017/1205
See application file for complete search history.

(56) References Cited

U.S. PATENT DOCUMENTS

| | | | |
|---|---|---|---|
| 3,840,018 A | 10/1974 | Heifetz | |
| 3,881,366 A | 5/1975 | Bradley et al. | |
| 3,898,701 A | 8/1975 | La Russa | |
| 4,042,979 A | 8/1977 | Angell | |
| 4,118,805 A | 10/1978 | Reimels | |
| 4,214,349 A | 7/1980 | Munch | |
| 4,261,342 A | 4/1981 | Aranguren Duo | |
| 4,290,151 A | 9/1981 | Massana | |
| 4,434,828 A | 3/1984 | Trincia | |
| 4,473,928 A | 10/1984 | Johnson | |
| 4,602,911 A | 7/1986 | Ahmadi et al. | |
| 4,625,727 A | 12/1986 | Leiboff | |
| 4,712,549 A | 12/1987 | Peters et al. | |
| 4,778,468 A | 10/1988 | Hunt et al. | |
| 4,917,698 A | 4/1990 | Carpentier et al. | |
| 4,961,738 A | 10/1990 | Mackin | |
| 5,042,707 A | 8/1991 | Taheri | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,108,420 A | 4/1992 | Marks | |
| 5,201,880 A | 4/1993 | Wright et al. | |
| 5,258,008 A | 11/1993 | Wilk | |
| 5,300,034 A | 4/1994 | Behnke et al. | |
| 5,325,845 A | 7/1994 | Adair | |
| 5,346,498 A | 9/1994 | Greelis et al. | |
| 5,383,852 A | 1/1995 | Stevens-Wright | |
| 5,449,368 A | 9/1995 | Kuzmak | |
| 5,450,860 A | 9/1995 | O'Connor | |
| 5,464,404 A | 11/1995 | Abela et al. | |
| 5,474,518 A | 12/1995 | Farrer Velazquez | |
| 5,477,856 A | 12/1995 | Lundquist | |
| 5,593,424 A | 1/1997 | Northrup, III | |
| 5,601,572 A | 2/1997 | Middleman et al. | |
| 5,626,609 A | 5/1997 | Zvenyatsky et al. | |
| 5,643,317 A | 7/1997 | Pavcnik et al. | |
| 5,669,919 A | 9/1997 | Sanders et al. | |
| 5,676,653 A | 10/1997 | Taylor et al. | |
| 5,683,402 A | 11/1997 | Cosgrove et al. | |
| 5,702,397 A | 12/1997 | Goble et al. | |
| 5,702,398 A | 12/1997 | Tarabishy | |
| 5,709,695 A | 1/1998 | Northrup, III | |
| 5,716,370 A | 2/1998 | Williamson, IV et al. | |
| 5,716,397 A | 2/1998 | Myers | |
| 5,728,116 A | 3/1998 | Rosenman | |
| 5,730,150 A | 3/1998 | Peppel et al. | |
| 5,749,371 A | 5/1998 | Zadini et al. | |
| 5,782,844 A | 7/1998 | Yoon et al. | |
| 5,810,882 A | 9/1998 | Bolduc et al. | |
| 5,824,066 A | 10/1998 | Gross | |
| 5,830,221 A | 11/1998 | Stein et al. | |
| 5,843,120 A | 12/1998 | Israel et al. | |
| 5,855,614 A | 1/1999 | Stevens et al. | |
| 5,865,791 A * | 2/1999 | Whayne | A61B 17/00234 604/500 |
| 5,876,373 A | 3/1999 | Giba et al. | |
| 5,935,098 A | 8/1999 | Blaisdell et al. | |
| 5,957,953 A | 9/1999 | DiPoto et al. | |
| 5,961,440 A | 10/1999 | Schweich, Jr. et al. | |
| 5,961,539 A | 10/1999 | Northrup, III et al. | |
| 5,984,959 A | 11/1999 | Robertson et al. | |
| 6,042,554 A | 3/2000 | Rosenman et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,074,341 A | 6/2000 | Anderson et al. | |
| 6,074,401 A | 6/2000 | Gardiner et al. | |
| 6,074,417 A | 6/2000 | Peredo | |
| 6,086,582 A | 7/2000 | Altman et al. | |
| 6,102,945 A | 8/2000 | Campbell | |
| 6,106,550 A | 8/2000 | Magovern et al. | |
| 6,110,200 A | 8/2000 | Hinnenkamp | |
| 6,132,390 A | 10/2000 | Cookston et al. | |
| 6,143,024 A | 11/2000 | Campbell et al. | |
| 6,159,240 A | 12/2000 | Sparer et al. | |
| 6,165,119 A | 12/2000 | Schweich, Jr. et al. | |
| 6,174,332 B1 | 1/2001 | Loch et al. | |
| 6,183,411 B1 | 2/2001 | Mortier et al. | |
| 6,187,040 B1 | 2/2001 | Wright | |
| 6,210,347 B1 | 4/2001 | Forsell | |
| 6,217,610 B1 | 4/2001 | Carpentier et al. | |
| 6,231,561 B1 * | 5/2001 | Frazier | A61B 17/00234 604/500 |
| 6,231,602 B1 | 5/2001 | Carpentier et al. | |
| 6,251,092 B1 | 6/2001 | Qin et al. | |
| 6,290,674 B1 * | 9/2001 | Roue | A61B 17/00234 604/107 |
| 6,296,656 B1 | 10/2001 | Bolduc et al. | |
| 6,315,784 B1 | 11/2001 | Djurovic | |
| 6,319,281 B1 | 11/2001 | Patel | |
| 6,328,727 B1 * | 12/2001 | Frazier | A61B 17/00234 604/107 |
| 6,328,746 B1 | 12/2001 | Gambale | |
| 6,332,893 B1 | 12/2001 | Mortier et al. | |
| 6,355,030 B1 | 3/2002 | Aldrich et al. | |
| 6,361,559 B1 | 3/2002 | Houser et al. | |
| 6,368,348 B1 | 4/2002 | Gabbay | |
| 6,402,780 B2 | 6/2002 | Williamson, IV et al. | |
| 6,406,420 B1 | 6/2002 | McCarthy | |
| 6,406,493 B1 | 6/2002 | Tu et al. | |
| 6,419,669 B1 * | 7/2002 | Frazier | A61B 17/00234 604/107 |
| 6,419,696 B1 | 7/2002 | Ortiz et al. | |
| 6,436,088 B2 * | 8/2002 | Frazier | A61B 17/00234 604/500 |
| 6,451,054 B1 | 9/2002 | Stevens | |
| 6,458,076 B1 | 10/2002 | Pruitt | |
| 6,458,100 B2 * | 10/2002 | Roue | A61B 17/00234 604/107 |
| 6,461,366 B1 | 10/2002 | Seguin | |
| 6,470,892 B1 | 10/2002 | Forsell | |
| 6,503,274 B1 | 1/2003 | Howanec, Jr. et al. | |
| 6,524,338 B1 | 2/2003 | Gundry | |
| 6,530,952 B2 | 3/2003 | Vesely | |
| 6,533,772 B1 | 3/2003 | Sherts et al. | |
| 6,537,314 B2 | 3/2003 | Langberg et al. | |
| 6,547,801 B1 | 4/2003 | Dargent et al. | |
| 6,554,845 B1 | 4/2003 | Fleenor et al. | |
| 6,561,969 B2 * | 5/2003 | Frazier | A61B 17/00234 128/898 |
| 6,564,805 B2 | 5/2003 | Garrison et al. | |
| 6,565,603 B2 | 5/2003 | Cox | |
| 6,569,198 B1 | 5/2003 | Wilson et al. | |
| 6,579,297 B2 | 6/2003 | Bicek et al. | |
| 6,589,160 B2 | 7/2003 | Schweich, Jr. et al. | |
| 6,592,593 B1 | 7/2003 | Parodi et al. | |
| 6,602,288 B1 | 8/2003 | Cosgrove et al. | |
| 6,602,289 B1 | 8/2003 | Colvin et al. | |
| 6,613,078 B1 | 9/2003 | Barone | |
| 6,613,079 B1 | 9/2003 | Wolinsky et al. | |
| 6,619,291 B2 | 9/2003 | Hlavka et al. | |
| 6,626,899 B2 | 9/2003 | Houser et al. | |
| 6,626,917 B1 | 9/2003 | Craig | |
| 6,626,930 B1 | 9/2003 | Allen et al. | |
| 6,629,534 B1 | 10/2003 | St Goar et al. | |
| 6,629,921 B1 | 10/2003 | Schweich, Jr. et al. | |
| 6,641,557 B1 * | 11/2003 | Frazier | A61B 17/00234 604/115 |
| 6,651,671 B1 | 11/2003 | Donlon et al. | |
| 6,652,556 B1 | 11/2003 | VanTassel et al. | |
| 6,682,558 B2 | 1/2004 | Tu et al. | |
| 6,689,125 B1 | 2/2004 | Keith et al. | |
| 6,689,164 B1 | 2/2004 | Seguin | |
| 6,695,866 B1 | 2/2004 | Kuehn et al. | |
| 6,702,825 B2 * | 3/2004 | Frazier | A61B 17/00234 606/139 |

(56) References Cited

U.S. PATENT DOCUMENTS

| | | | |
|---|---|---|---|
| 6,702,826 B2 | 3/2004 | Liddicoat et al. | |
| 6,702,846 B2 | 3/2004 | Mikus et al. | |
| 6,706,065 B2 | 3/2004 | Langberg et al. | |
| 6,709,385 B2 | 3/2004 | Forsell | |
| 6,709,456 B2 | 3/2004 | Langberg et al. | |
| 6,711,444 B2 | 3/2004 | Koblish | |
| 6,712,804 B2* | 3/2004 | Roue | A61B 17/00234 604/107 |
| 6,719,786 B2 | 4/2004 | Ryan et al. | |
| 6,723,038 B1 | 4/2004 | Schroeder et al. | |
| 6,726,716 B2 | 4/2004 | Marquez | |
| 6,726,717 B2 | 4/2004 | Alfieri et al. | |
| 6,730,121 B2 | 5/2004 | Ortiz et al. | |
| 6,746,472 B2* | 6/2004 | Frazier | A61B 17/00234 606/232 |
| 6,749,630 B2 | 6/2004 | McCarthy et al. | |
| 6,752,813 B2 | 6/2004 | Goldfarb et al. | |
| 6,764,310 B1 | 7/2004 | Ichihashi et al. | |
| 6,764,510 B2 | 7/2004 | Vidlund et al. | |
| 6,764,810 B2 | 7/2004 | Ma et al. | |
| 6,770,083 B2 | 8/2004 | Seguin | |
| 6,786,924 B2 | 9/2004 | Ryan et al. | |
| 6,786,925 B1 | 9/2004 | Schoon et al. | |
| 6,790,231 B2 | 9/2004 | Liddicoat et al. | |
| 6,797,001 B2 | 9/2004 | Mathis et al. | |
| 6,797,002 B2 | 9/2004 | Spence et al. | |
| 6,802,319 B2 | 10/2004 | Stevens et al. | |
| 6,805,710 B2 | 10/2004 | Bolling et al. | |
| 6,805,711 B2 | 10/2004 | Quijano et al. | |
| 6,855,126 B2 | 2/2005 | Flinchbaugh | |
| 6,858,039 B2 | 2/2005 | McCarthy | |
| 6,884,250 B2 | 4/2005 | Monassevitch et al. | |
| 6,893,459 B1 | 5/2005 | Macoviak | |
| 6,908,478 B2 | 6/2005 | Alferness et al. | |
| 6,908,482 B2 | 6/2005 | McCarthy et al. | |
| 6,918,917 B1 | 7/2005 | Nguyen et al. | |
| 6,926,730 B1 | 8/2005 | Nguyen et al. | |
| 6,960,217 B2 | 11/2005 | Bolduc | |
| 6,964,684 B2 | 11/2005 | Ortiz et al. | |
| 6,964,686 B2 | 11/2005 | Gordon | |
| 6,976,995 B2 | 12/2005 | Mathis et al. | |
| 6,986,775 B2 | 1/2006 | Morales et al. | |
| 6,989,028 B2 | 1/2006 | Lashinski et al. | |
| 6,997,951 B2 | 2/2006 | Solem et al. | |
| 7,004,176 B2 | 2/2006 | Lau | |
| 7,007,798 B2 | 3/2006 | Happonen et al. | |
| 7,011,669 B2 | 3/2006 | Kimblad | |
| 7,011,682 B2 | 3/2006 | Lashinski et al. | |
| 7,018,406 B2 | 3/2006 | Seguin et al. | |
| 7,025,756 B2* | 4/2006 | Frazier | A61B 17/00234 604/500 |
| 7,037,334 B1 | 5/2006 | Hlavka et al. | |
| 7,087,064 B1 | 6/2006 | Hyde | |
| 7,077,850 B2 | 7/2006 | Kortenbach | |
| 7,077,862 B2 | 7/2006 | Vidlund et al. | |
| 7,101,395 B2 | 9/2006 | Tremulis et al. | |
| 7,101,396 B2 | 9/2006 | Artof et al. | |
| 7,112,207 B2 | 9/2006 | Allen et al. | |
| 7,115,110 B2* | 10/2006 | Frazier | A61B 17/00234 604/115 |
| 7,118,595 B2 | 10/2006 | Ryan et al. | |
| 7,125,421 B2 | 10/2006 | Tremulis et al. | |
| 7,150,737 B2 | 12/2006 | Purdy et al. | |
| 7,159,593 B2 | 1/2007 | McCarthy et al. | |
| 7,166,127 B2 | 1/2007 | Spence et al. | |
| 7,169,187 B2 | 1/2007 | Datta et al. | |
| 7,172,625 B2 | 2/2007 | Shu et al. | |
| 7,175,660 B2 | 2/2007 | Cartledge et al. | |
| 7,186,262 B2 | 3/2007 | Saadat | |
| 7,186,264 B2 | 3/2007 | Liddicoat et al. | |
| 7,189,199 B2 | 3/2007 | McCarthy et al. | |
| 7,192,443 B2 | 3/2007 | Solem et al. | |
| 7,220,277 B2 | 5/2007 | Arru et al. | |
| 7,226,467 B2 | 6/2007 | Lucatero et al. | |
| 7,226,477 B2 | 6/2007 | Cox | |
| 7,226,647 B2 | 6/2007 | Kasperchik et al. | |
| 7,229,452 B2 | 6/2007 | Kayan | |
| 7,238,191 B2 | 7/2007 | Bachmann | |
| 7,288,097 B2 | 10/2007 | Seguin | |
| 7,294,148 B2 | 11/2007 | McCarthy | |
| 7,311,728 B2 | 12/2007 | Solem et al. | |
| 7,311,729 B2 | 12/2007 | Mathis et al. | |
| 7,314,485 B2 | 1/2008 | Mathis | |
| 7,316,710 B1 | 1/2008 | Cheng et al. | |
| 7,329,279 B2 | 2/2008 | Haug et al. | |
| 7,329,280 B2 | 2/2008 | Bolling et al. | |
| 7,335,213 B1 | 2/2008 | Hyde et al. | |
| 7,361,190 B2 | 4/2008 | Shaoulian et al. | |
| 7,364,588 B2 | 4/2008 | Mathis et al. | |
| 7,377,941 B2 | 5/2008 | Rhee et al. | |
| 7,390,329 B2 | 6/2008 | Westra et al. | |
| 7,404,824 B1 | 7/2008 | Webler et al. | |
| 7,427,279 B2* | 9/2008 | Frazier | A61B 17/00234 604/115 |
| 7,431,692 B2 | 10/2008 | Zollinger et al. | |
| 7,442,207 B2 | 10/2008 | Rafiee | |
| 7,452,376 B2 | 11/2008 | Lim et al. | |
| 7,455,690 B2 | 11/2008 | Cartledge et al. | |
| 7,485,142 B2 | 2/2009 | Milo | |
| 7,485,143 B2 | 2/2009 | Webler et al. | |
| 7,500,989 B2 | 3/2009 | Solem et al. | |
| 7,507,252 B2 | 3/2009 | Lashinski et al. | |
| 7,510,575 B2 | 3/2009 | Spenser et al. | |
| 7,510,577 B2 | 3/2009 | Moaddeb et al. | |
| 7,527,647 B2 | 5/2009 | Spence | |
| 7,530,995 B2 | 5/2009 | Quijano et al. | |
| 7,549,983 B2* | 6/2009 | Roue | A61B 17/00234 604/107 |
| 7,559,936 B2 | 7/2009 | Levine | |
| 7,562,660 B2 | 7/2009 | Saadat | |
| 7,563,267 B2 | 7/2009 | Goldfarb et al. | |
| 7,563,273 B2 | 7/2009 | Goldfarb et al. | |
| 7,569,062 B1 | 8/2009 | Kuehn et al. | |
| 7,585,321 B2 | 9/2009 | Cribier | |
| 7,588,582 B2 | 9/2009 | Starksen et al. | |
| 7,591,826 B2 | 9/2009 | Alferness et al. | |
| 7,604,646 B2 | 10/2009 | Goldfarb et al. | |
| 7,608,091 B2 | 10/2009 | Goldfarb et al. | |
| 7,608,103 B2 | 10/2009 | McCarthy | |
| 7,625,403 B2 | 12/2009 | Krivoruchko | |
| 7,632,303 B1 | 12/2009 | Stalker et al. | |
| 7,635,329 B2 | 12/2009 | Goldfarb et al. | |
| 7,635,386 B1 | 12/2009 | Gammie | |
| 7,655,015 B2 | 2/2010 | Goldfarb et al. | |
| 7,666,204 B2 | 2/2010 | Thornton et al. | |
| 7,682,319 B2 | 3/2010 | Martin et al. | |
| 7,682,369 B2 | 3/2010 | Seguin | |
| 7,686,822 B2 | 3/2010 | Shayani | |
| 7,699,892 B2 | 4/2010 | Rafiee et al. | |
| 7,704,269 B2 | 4/2010 | St. Goar et al. | |
| 7,704,277 B2 | 4/2010 | Zakay et al. | |
| 7,722,641 B2* | 5/2010 | van der Burg | A61B 17/0057 606/142 |
| 7,722,666 B2 | 5/2010 | Lafontaine | |
| 7,736,388 B2 | 6/2010 | Goldfarb et al. | |
| 7,748,389 B2 | 7/2010 | Salahieh et al. | |
| 7,753,924 B2 | 7/2010 | Starksen et al. | |
| 7,758,632 B2 | 7/2010 | Hojeibane et al. | |
| 7,780,683 B2* | 8/2010 | Roue | A61B 17/00234 606/144 |
| 7,780,726 B2 | 8/2010 | Seguin | |
| 7,871,368 B2 | 1/2011 | Zollinger et al. | |
| 7,871,433 B2 | 1/2011 | Lattouf | |
| 7,883,475 B2 | 2/2011 | Dupont et al. | |
| 7,883,538 B2 | 2/2011 | To et al. | |
| 7,892,281 B2 | 2/2011 | Seguin et al. | |
| 7,927,370 B2 | 4/2011 | Webler et al. | |
| 7,927,371 B2 | 4/2011 | Navia et al. | |
| 7,942,927 B2 | 5/2011 | Kaye et al. | |
| 7,947,056 B2 | 5/2011 | Griego et al. | |
| 7,955,315 B2 | 6/2011 | Feinberg et al. | |
| 7,955,377 B2 | 6/2011 | Melsheimer | |
| 7,992,567 B2 | 6/2011 | Hirotsuka et al. | |
| 7,993,368 B2 | 8/2011 | Gambale et al. | |

(56) References Cited

U.S. PATENT DOCUMENTS

| | | | |
|---|---|---|---|
| 7,993,397 B2 | 8/2011 | Lashinski et al. | |
| 8,012,201 B2 | 9/2011 | Lashinski et al. | |
| 8,034,103 B2 | 10/2011 | Burriesci et al. | |
| 8,043,305 B2 * | 10/2011 | Frazier | A61B 17/00234 606/139 |
| 8,052,592 B2 | 11/2011 | Goldfarb et al. | |
| 8,057,493 B2 | 11/2011 | Goldfarb et al. | |
| 8,062,355 B2 | 11/2011 | Figulla et al. | |
| 8,070,804 B2 | 12/2011 | Hyde et al. | |
| 8,070,805 B2 | 12/2011 | Vidlund et al. | |
| 8,075,616 B2 | 12/2011 | Solem et al. | |
| 8,100,964 B2 | 1/2012 | Spence | |
| 8,123,801 B2 | 2/2012 | Milo | |
| 8,142,493 B2 | 3/2012 | Spence et al. | |
| 8,142,495 B2 | 3/2012 | Hasenkam et al. | |
| 8,142,496 B2 | 3/2012 | Berreklouw | |
| 8,147,542 B2 | 4/2012 | Maisano et al. | |
| 8,152,844 B2 | 4/2012 | Rao et al. | |
| 8,163,013 B2 | 4/2012 | Machold et al. | |
| 8,187,299 B2 | 5/2012 | Goldfarb et al. | |
| 8,187,324 B2 | 5/2012 | Webler et al. | |
| 8,197,496 B2 * | 6/2012 | Roue | A61B 17/00234 606/144 |
| 8,202,315 B2 | 6/2012 | Hlavka et al. | |
| 8,206,439 B2 | 6/2012 | Gomez Duran | |
| 8,216,302 B2 | 7/2012 | Wilson et al. | |
| 8,221,384 B2 * | 7/2012 | Frazier | A61B 17/00234 604/500 |
| 8,231,671 B2 | 7/2012 | Kim | |
| 8,262,725 B2 | 9/2012 | Subramanian | |
| 8,265,758 B2 | 9/2012 | Policker et al. | |
| 8,277,502 B2 | 10/2012 | Miller et al. | |
| 8,287,584 B2 | 10/2012 | Salahieh et al. | |
| 8,287,591 B2 | 10/2012 | Keidar et al. | |
| 8,292,884 B2 | 10/2012 | Levine et al. | |
| 8,303,608 B2 | 11/2012 | Goldfarb et al. | |
| 8,323,334 B2 | 12/2012 | Deem et al. | |
| 8,328,868 B2 | 12/2012 | Paul et al. | |
| 8,333,777 B2 | 12/2012 | Schaller et al. | |
| 8,343,173 B2 | 1/2013 | Starksen et al. | |
| 8,343,174 B2 | 1/2013 | Goldfarb et al. | |
| 8,343,213 B2 | 1/2013 | Salahieh et al. | |
| 8,349,002 B2 | 1/2013 | Milo | |
| 8,353,956 B2 | 1/2013 | Miller et al. | |
| 8,357,195 B2 | 1/2013 | Kuehn | |
| 8,382,829 B1 | 2/2013 | Call et al. | |
| 8,388,680 B2 | 3/2013 | Starksen et al. | |
| 8,393,517 B2 | 3/2013 | Milo | |
| 8,419,825 B2 | 4/2013 | Burgler et al. | |
| 8,430,926 B2 | 4/2013 | Kirson | |
| 8,449,573 B2 | 5/2013 | Chu | |
| 8,449,599 B2 | 5/2013 | Chau et al. | |
| 8,454,686 B2 | 6/2013 | Alkhatib | |
| 8,460,370 B2 | 6/2013 | Zakay | |
| 8,460,371 B2 | 6/2013 | Hlavka et al. | |
| 8,475,491 B2 | 7/2013 | Milo | |
| 8,475,525 B2 | 7/2013 | Maisano et al. | |
| 8,480,732 B2 | 7/2013 | Subramanian | |
| 8,518,107 B2 | 8/2013 | Tsukashima et al. | |
| 8,523,940 B2 | 9/2013 | Richardson et al. | |
| 8,551,161 B2 | 10/2013 | Dolan | |
| 8,585,755 B2 | 11/2013 | Chau et al. | |
| 8,591,576 B2 | 11/2013 | Hasenkam et al. | |
| 8,603,108 B2 * | 12/2013 | Roue | A61B 17/00234 606/139 |
| 8,608,797 B2 | 12/2013 | Gross et al. | |
| 8,628,569 B2 | 1/2014 | Benichou et al. | |
| 8,628,571 B1 | 1/2014 | Hacohen et al. | |
| 8,641,727 B2 | 2/2014 | Starksen et al. | |
| 8,652,202 B2 | 2/2014 | Alon et al. | |
| 8,652,203 B2 | 2/2014 | Quadri et al. | |
| 8,679,174 B2 | 3/2014 | Ottma et al. | |
| 8,685,086 B2 | 4/2014 | Navia et al. | |
| 8,728,097 B1 | 5/2014 | Sugimoto et al. | |
| 8,728,155 B2 | 5/2014 | Montorfano et al. | |
| 8,734,467 B2 | 5/2014 | Miller et al. | |
| 8,734,699 B2 | 5/2014 | Heideman et al. | |
| 8,740,920 B2 | 6/2014 | Goldfarb et al. | |
| 8,747,463 B2 | 6/2014 | Fogarty et al. | |
| 8,778,021 B2 | 7/2014 | Cartledge | |
| 8,784,481 B2 | 7/2014 | Alkhatib et al. | |
| 8,790,367 B2 | 7/2014 | Nguyen et al. | |
| 8,790,394 B2 | 7/2014 | Miller et al. | |
| 8,795,298 B2 | 8/2014 | Hernlund et al. | |
| 8,795,355 B2 | 8/2014 | Alkhatib | |
| 8,795,356 B2 | 8/2014 | Quadri et al. | |
| 8,795,357 B2 | 8/2014 | Yohanan et al. | |
| 8,808,366 B2 | 8/2014 | Braido et al. | |
| 8,808,368 B2 | 8/2014 | Maisano et al. | |
| 8,645,723 B2 | 9/2014 | Spence et al. | |
| 8,845,717 B2 | 9/2014 | Khairkhahan et al. | |
| 8,852,261 B2 | 10/2014 | White | |
| 8,852,272 B2 | 10/2014 | Gross et al. | |
| 8,858,623 B2 | 10/2014 | Miller et al. | |
| 8,864,822 B2 | 10/2014 | Spence et al. | |
| 8,870,948 B1 | 10/2014 | Erzberger et al. | |
| 8,870,949 B2 | 10/2014 | Rowe | |
| 8,888,843 B2 | 11/2014 | Khairkhahan et al. | |
| 8,889,861 B2 | 11/2014 | Skead et al. | |
| 8,894,702 B2 | 11/2014 | Quadri et al. | |
| 8,911,461 B2 | 12/2014 | Traynor et al. | |
| 8,911,494 B2 | 12/2014 | Hammer et al. | |
| 8,926,696 B2 | 1/2015 | Cabiri et al. | |
| 8,926,697 B2 | 1/2015 | Gross et al. | |
| 8,932,343 B2 | 1/2015 | Alkhatib et al. | |
| 8,932,348 B2 | 1/2015 | Solem et al. | |
| 8,940,044 B2 | 1/2015 | Hammer et al. | |
| 8,945,211 B2 | 2/2015 | Sugimoto | |
| 8,951,285 B2 | 2/2015 | Sugimoto et al. | |
| 8,951,286 B2 | 2/2015 | Sugimoto et al. | |
| 8,961,595 B2 | 2/2015 | Alkhatib | |
| 8,961,602 B2 | 2/2015 | Kovach et al. | |
| 8,979,922 B2 | 3/2015 | Jayasinghe et al. | |
| 8,992,604 B2 | 3/2015 | Gross et al. | |
| 9,005,273 B2 | 4/2015 | Salahieh et al. | |
| 9,011,520 B2 | 4/2015 | Miller et al. | |
| 9,011,530 B2 | 4/2015 | Reich et al. | |
| 9,023,100 B2 | 5/2015 | Quadri et al. | |
| 9,072,603 B2 | 7/2015 | Tuval et al. | |
| 9,089,313 B2 * | 7/2015 | Roue | A61B 17/00234 |
| 9,107,749 B2 | 8/2015 | Bobo et al. | |
| 9,119,719 B2 | 9/2015 | Zipory et al. | |
| 9,125,632 B2 | 9/2015 | Loulmet et al. | |
| 9,125,742 B2 | 9/2015 | Yoganathan et al. | |
| 9,138,316 B2 | 9/2015 | Bielefeld | |
| 9,173,646 B2 | 11/2015 | Fabro | |
| 9,180,005 B1 | 11/2015 | Lashinski et al. | |
| 9,180,007 B2 | 11/2015 | Reich et al. | |
| 9,192,472 B2 | 11/2015 | Gross et al. | |
| 9,198,756 B2 | 12/2015 | Aklog et al. | |
| 9,226,825 B2 | 1/2016 | Starksen et al. | |
| 9,259,218 B2 | 2/2016 | Robinson | |
| 9,265,608 B2 | 2/2016 | Miller et al. | |
| 9,326,857 B2 | 5/2016 | Cartledge et al. | |
| 9,358,111 B2 * | 6/2016 | Spence | A61B 17/00234 |
| 9,414,921 B2 | 8/2016 | Miller et al. | |
| 9,421,004 B2 * | 8/2016 | Roue | A61B 17/00234 |
| 9,427,316 B2 | 8/2016 | Schweich, Jr. et al. | |
| 9,474,606 B2 | 10/2016 | Zipory et al. | |
| 9,526,613 B2 | 12/2016 | Gross et al. | |
| 9,561,104 B2 | 2/2017 | Miller et al. | |
| 9,693,865 B2 | 7/2017 | Gilmore et al. | |
| 9,730,793 B2 | 8/2017 | Reich et al. | |
| 9,788,941 B2 | 10/2017 | Hacohen | |
| 9,801,720 B2 | 10/2017 | Gilmore et al. | |
| 9,907,547 B2 | 3/2018 | Gilmore et al. | |
| 10,368,852 B2 | 8/2019 | Gerhardt et al. | |
| 2001/0014800 A1 * | 8/2001 | Frazier | A61B 17/00234 604/508 |
| 2001/0021874 A1 | 9/2001 | Carpentier et al. | |
| 2001/0039434 A1 * | 11/2001 | Frazier | A61B 17/00234 606/213 |
| 2001/0039435 A1 * | 11/2001 | Roue | A61B 17/00234 606/216 |

(56) References Cited

U.S. PATENT DOCUMENTS

| | | | |
|---|---|---|---|
| 2001/0039436 A1* | 11/2001 | Frazier | A61B 17/00234 606/219 |
| 2001/0041915 A1* | 11/2001 | Roue | A61B 17/00234 606/225 |
| 2001/0049492 A1* | 12/2001 | Frazier | A61B 17/00234 604/104 |
| 2002/0022862 A1 | 2/2002 | Grafton et al. | |
| 2002/0082525 A1 | 6/2002 | Oslund et al. | |
| 2002/0087048 A1 | 7/2002 | Brock et al. | |
| 2002/0103532 A1 | 8/2002 | Langberg et al. | |
| 2002/0151916 A1 | 10/2002 | Muramatsu et al. | |
| 2002/0151970 A1 | 10/2002 | Garrison et al. | |
| 2002/0169358 A1 | 11/2002 | Mortier et al. | |
| 2002/0177904 A1 | 11/2002 | Huxel et al. | |
| 2002/0188301 A1 | 12/2002 | Dallara et al. | |
| 2002/0188350 A1 | 12/2002 | Arru et al. | |
| 2002/0198586 A1 | 12/2002 | Inoue | |
| 2003/0050693 A1 | 3/2003 | Quijano et al. | |
| 2003/0078465 A1 | 4/2003 | Pai et al. | |
| 2003/0078653 A1 | 4/2003 | Vesely et al. | |
| 2003/0105519 A1 | 6/2003 | Fasol et al. | |
| 2003/0114901 A1 | 6/2003 | Loeb et al. | |
| 2003/0120340 A1 | 6/2003 | Liska et al. | |
| 2003/0144657 A1 | 7/2003 | Bowe et al. | |
| 2003/0171760 A1 | 9/2003 | Gambale | |
| 2003/0199974 A1 | 10/2003 | Lee et al. | |
| 2003/0204195 A1 | 10/2003 | Keane et al. | |
| 2003/0229350 A1 | 12/2003 | Kay | |
| 2003/0229395 A1 | 12/2003 | Cox | |
| 2004/0010287 A1 | 1/2004 | Bonutti | |
| 2004/0019359 A1 | 1/2004 | Worley et al. | |
| 2004/0019377 A1 | 1/2004 | Taylor et al. | |
| 2004/0024451 A1 | 2/2004 | Johnson et al. | |
| 2004/0039442 A1 | 2/2004 | St. Goar et al. | |
| 2004/0059413 A1 | 3/2004 | Argento | |
| 2004/0098047 A1* | 5/2004 | Frazier | A61B 17/00234 606/222 |
| 2004/0122514 A1 | 6/2004 | Fogarty et al. | |
| 2004/0127982 A1 | 7/2004 | Machold et al. | |
| 2004/0133274 A1 | 7/2004 | Webler et al. | |
| 2004/0133374 A1 | 7/2004 | Kattan | |
| 2004/0138744 A1 | 7/2004 | Lashinski et al. | |
| 2004/0138745 A1 | 7/2004 | Macoviak et al. | |
| 2004/0148019 A1 | 7/2004 | Vidlund et al. | |
| 2004/0148020 A1 | 7/2004 | Vidlund et al. | |
| 2004/0148021 A1 | 7/2004 | Cartledge et al. | |
| 2004/0176788 A1 | 9/2004 | Opolski | |
| 2004/0181287 A1 | 9/2004 | Gellman | |
| 2004/0186486 A1* | 9/2004 | Roue | A61B 17/00234 606/139 |
| 2004/0186566 A1 | 9/2004 | Hindrichs et al. | |
| 2004/0193191 A1 | 9/2004 | Starksen et al. | |
| 2004/0220595 A1* | 11/2004 | Frazier | A61B 17/00234 606/151 |
| 2004/0243227 A1 | 12/2004 | Starksen et al. | |
| 2004/0260317 A1 | 12/2004 | Bloom et al. | |
| 2004/0260393 A1 | 12/2004 | Rahdert et al. | |
| 2004/0260394 A1 | 12/2004 | Douk et al. | |
| 2004/0267358 A1 | 12/2004 | Reitan | |
| 2005/0004668 A1 | 1/2005 | Aklog et al. | |
| 2005/0010287 A1 | 1/2005 | Macoviak et al. | |
| 2005/0010787 A1 | 1/2005 | Tarbouriech | |
| 2005/0016560 A1 | 1/2005 | Voughlohn | |
| 2005/0049692 A1 | 3/2005 | Numamoto et al. | |
| 2005/0055038 A1 | 3/2005 | Kelleher et al. | |
| 2005/0055087 A1 | 3/2005 | Starksen | |
| 2005/0060030 A1 | 3/2005 | Lashinski et al. | |
| 2005/0065601 A1 | 3/2005 | Lee et al. | |
| 2005/0070999 A1 | 3/2005 | Spence | |
| 2005/0075727 A1 | 4/2005 | Wheatley | |
| 2005/0090627 A1 | 4/2005 | Gedebou | |
| 2005/0090834 A1 | 4/2005 | Chiang et al. | |
| 2005/0096740 A1 | 5/2005 | Langberg et al. | |
| 2005/0107871 A1 | 5/2005 | Realyvasquez et al. | |
| 2005/0119734 A1 | 6/2005 | Spence et al. | |
| 2005/0125002 A1 | 6/2005 | Baran et al. | |
| 2005/0125011 A1 | 6/2005 | Spence et al. | |
| 2005/0131533 A1 | 6/2005 | Alfieri et al. | |
| 2005/0137686 A1 | 6/2005 | Salahieh et al. | |
| 2005/0137688 A1 | 6/2005 | Salahieh et al. | |
| 2005/0137695 A1 | 6/2005 | Salahieh et al. | |
| 2005/0149115 A1* | 7/2005 | Roue | A61B 17/00234 606/213 |
| 2005/0159728 A1 | 7/2005 | Armour et al. | |
| 2005/0171601 A1 | 8/2005 | Cosgrove et al. | |
| 2005/0177180 A1 | 8/2005 | Kaganov et al. | |
| 2005/0177228 A1 | 8/2005 | Solem et al. | |
| 2005/0187568 A1 | 8/2005 | Klenk et al. | |
| 2005/0192596 A1 | 9/2005 | Jugenheimer et al. | |
| 2005/0203549 A1 | 9/2005 | Realyvasquez | |
| 2005/0203606 A1 | 9/2005 | VanCamp | |
| 2005/0216039 A1 | 9/2005 | Lederman | |
| 2005/0216079 A1 | 9/2005 | MaCoviak | |
| 2005/0222665 A1 | 10/2005 | Aranyi | |
| 2005/0256532 A1 | 11/2005 | Nayak et al. | |
| 2005/0267478 A1 | 12/2005 | Corradi et al. | |
| 2005/0273138 A1 | 12/2005 | To et al. | |
| 2005/0288778 A1 | 12/2005 | Shaoulian et al. | |
| 2006/0004442 A1 | 1/2006 | Spenser et al. | |
| 2006/0004443 A1 | 1/2006 | Liddicoat et al. | |
| 2006/0020326 A9 | 1/2006 | Bolduc et al. | |
| 2006/0020327 A1 | 1/2006 | Lashinski et al. | |
| 2006/0020333 A1 | 1/2006 | Lashinski et al. | |
| 2006/0020336 A1 | 1/2006 | Liddicoat | |
| 2006/0025658 A1 | 2/2006 | Alameddine | |
| 2006/0025787 A1 | 2/2006 | Morales et al. | |
| 2006/0030885 A1 | 2/2006 | Hyde | |
| 2006/0041319 A1 | 2/2006 | Taylor et al. | |
| 2006/0069429 A1 | 3/2006 | Spence et al. | |
| 2006/0074486 A1 | 4/2006 | Liddicoat et al. | |
| 2006/0085012 A1 | 4/2006 | Dolan | |
| 2006/0095009 A1 | 5/2006 | Lampropoulos et al. | |
| 2006/0106423 A1 | 5/2006 | Weisel et al. | |
| 2006/0116757 A1 | 6/2006 | Lashinski et al. | |
| 2006/0122633 A1 | 6/2006 | To et al. | |
| 2006/0129166 A1 | 6/2006 | Lavelle | |
| 2006/0149280 A1 | 7/2006 | Harvie et al. | |
| 2006/0149368 A1 | 7/2006 | Spence | |
| 2006/0161265 A1 | 7/2006 | Levine et al. | |
| 2006/0184202 A1* | 8/2006 | Frazier | A61B 17/00234 606/232 |
| 2006/0184234 A1* | 8/2006 | Frazier | A61B 17/00234 623/1.36 |
| 2006/0184240 A1 | 8/2006 | Jimenez et al. | |
| 2006/0184242 A1 | 8/2006 | Lichtenstein | |
| 2006/0195134 A1 | 8/2006 | Crittenden | |
| 2006/0206203 A1 | 9/2006 | Yang et al. | |
| 2006/0241622 A1 | 10/2006 | Zergiebel | |
| 2006/0241656 A1 | 10/2006 | Starksen et al. | |
| 2006/0241748 A1 | 10/2006 | Lee et al. | |
| 2006/0247763 A1 | 11/2006 | Slater | |
| 2006/0253129 A1* | 11/2006 | Liddicoat | A61B 17/00234 606/139 |
| 2006/0259135 A1 | 11/2006 | Navia et al. | |
| 2006/0271175 A1 | 11/2006 | Woolfson et al. | |
| 2006/0282161 A1 | 12/2006 | Huynh et al. | |
| 2006/0287661 A1* | 12/2006 | Bolduc | A61B 17/00234 606/153 |
| 2006/0287716 A1 | 12/2006 | Banbury et al. | |
| 2007/0001627 A1 | 1/2007 | Lin et al. | |
| 2007/0016287 A1 | 1/2007 | Cartledge et al. | |
| 2007/0016288 A1 | 1/2007 | Gurskis et al. | |
| 2007/0021781 A1 | 1/2007 | Jervis et al. | |
| 2007/0027533 A1 | 2/2007 | Douk | |
| 2007/0027536 A1 | 2/2007 | Mihaljevic et al. | |
| 2007/0038221 A1 | 2/2007 | Fine et al. | |
| 2007/0038293 A1 | 2/2007 | St.Goar et al. | |
| 2007/0038296 A1 | 2/2007 | Navia et al. | |
| 2007/0039425 A1 | 2/2007 | Wang | |
| 2007/0043344 A1* | 2/2007 | McAuley | A61B 17/12122 606/27 |
| 2007/0049942 A1 | 3/2007 | Hindrichs et al. | |
| 2007/0049970 A1 | 3/2007 | Belef et al. | |

(56) References Cited

U.S. PATENT DOCUMENTS

| | | |
|---|---|---|
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0073313 A1* | 3/2007 | Liddicoat ......... A61B 17/12009 606/139 |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083227 A1* | 4/2007 | van der Burg ..... A61B 17/0057 606/200 |
| 2007/0083232 A1* | 4/2007 | Lee ................. A61B 17/0057 606/213 |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0265641 A1* | 11/2007 | Roue ................. A61B 17/00234 606/139 |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033241 A1* | 2/2008 | Peh ..................... A61B 1/0008 600/109 |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0147097 A1* | 6/2008 | Liddicoat ......... A61B 17/12009 606/148 |
| 2008/0195200 A1 | 6/2008 | Vidlund et al. |
| 2008/0167713 A1 | 7/2008 | Bolling |
| 2008/0167714 A1 | 7/2008 | St. Goar et al. |
| 2008/0195126 A1 | 8/2008 | Solem |
| 2008/0208265 A1 | 8/2008 | Frazier et al. |
| 2008/0221593 A1* | 9/2008 | Liddicoat ......... A61B 17/12009 606/144 |
| 2008/0221672 A1 | 9/2008 | Lamphere et al. |
| 2008/0228265 A1* | 9/2008 | Spence ............ A61B 17/00234 623/2.36 |
| 2008/0228266 A1* | 9/2008 | McNamara ...... A61B 17/00234 623/2.36 |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0112249 A1* | 4/2009 | Miles ............... A61B 17/12122 606/192 |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152645 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0046622 A1* | 2/2011 | McAuley ......... A61B 17/12122 606/41 |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144660 A1* | 6/2011 | Liddicoat ......... A61B 17/00234 606/139 |
| 2011/0144703 A1 | 6/2011 | Krause et al. |

(56) References Cited

U.S. PATENT DOCUMENTS

| | | |
|---|---|---|
| 2011/0202130 A1 | 8/2011 | Cartledge et al. |
| 2011/0208283 A1 | 8/2011 | Rust |
| 2011/0218566 A1* | 9/2011 | van der Burg ..... A61B 17/0057 606/200 |
| 2011/0230941 A1 | 9/2011 | Markus |
| 2011/0230961 A1 | 9/2011 | Langer et al. |
| 2011/0238088 A1* | 9/2011 | Bolduc ............ A61B 17/00234 606/139 |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2011/0301595 A1* | 12/2011 | McAuley ......... A61B 17/12122 606/41 |
| 2012/0029541 A1* | 2/2012 | Frazier ............. A61B 17/00234 606/153 |
| 2012/0065662 A1* | 3/2012 | van der Burg ..... A61B 17/0057 606/200 |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0116269 A1* | 5/2012 | McAuley ......... A61B 17/12122 601/2 |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0232585 A1* | 9/2012 | Roue ................ A61B 17/00234 606/213 |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331884 A1* | 12/2013 | Van der Burg .... A61B 17/0057 606/200 |
| 2014/0046360 A1* | 2/2014 | van der Burg ..... A61B 17/0057 606/200 |
| 2014/0081394 A1 | 3/2014 | Keranen et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1* | 4/2014 | Spence ............. A61B 17/00234 623/2.36 |
| 2014/0100606 A1* | 4/2014 | Roue ................ A61B 17/00234 606/213 |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0336699 A1* | 11/2014 | van der Burg ..... A61B 17/0057 606/213 |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0066074 A1* | 3/2015 | Miles ............... A61B 17/12122 606/200 |
| 2015/0081014 A1 | 3/2015 | Gross et al. |
| 2015/0112432 A1 | 4/2015 | Reich et al. |
| 2015/0127097 A1 | 5/2015 | Neumann et al. |
| 2015/0173740 A1 | 6/2015 | Sugimoto et al. |
| 2015/0182336 A1 | 7/2015 | Zipory et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0313604 A1* | 11/2015 | Roue ................ A61B 17/00234 606/139 |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0106437 A1* | 4/2016 | van der Burg ..... A61B 17/0057 606/200 |
| 2016/0113767 A1 | 4/2016 | Miller et al. |
| 2016/0120645 A1 | 5/2016 | Alon |
| 2016/0158008 A1 | 6/2016 | Miller et al. |
| 2016/0235412 A1* | 8/2016 | Liddicoat ......... A61B 17/12009 |
| 2016/0242762 A1 | 8/2016 | Gilmore et al. |
| 2016/0262755 A1 | 9/2016 | Zipory et al. |
| 2016/0270916 A1 | 9/2016 | Cahalane et al. |
| 2016/0302917 A1 | 10/2016 | Schewel |
| 2016/0317302 A1 | 11/2016 | Madjarov et al. |
| 2016/0317304 A1* | 11/2016 | Spence ............ A61B 17/00234 |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0100112 A1* | 4/2017 | van der Burg ..... A61B 17/0057 |
| 2017/0189072 A1* | 7/2017 | Sutherland ............ A61F 2/2481 |
| 2017/0224489 A1 | 8/2017 | Starksen et al. |
| 2017/0245993 A1 | 8/2017 | Gross et al. |
| 2017/0290591 A1* | 10/2017 | Liddicoat ......... A61B 17/12009 |
| 2017/0340329 A1* | 11/2017 | Groothuis ........ A61B 17/12013 |
| 2018/0000487 A1* | 1/2018 | Miles ............... A61B 17/12122 |
| 2018/0049875 A1 | 2/2018 | Iflah et al. |
| 2018/0318080 A1 | 11/2018 | Quill et al. |
| 2019/0038411 A1 | 2/2019 | Alon |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |

(56) References Cited

FOREIGN PATENT DOCUMENTS

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, Ali et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZERT® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success—midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence, Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

METHOD AND SYSTEM FOR CLOSING LEFT ATRIAL APPENDAGE

CROSS-REFERENCE TO RELATED PATENT APPLICATIONS

This application is based on and claims priority to U.S. Provisional Patent Application 62/342,187, filed May 26, 2016, the entire contents of which is incorporated by reference herein as if expressly set forth in its respective entirety herein.

TECHNICAL FIELD

The present teachings generally relate to a treatment system and its use in reshaping, reducing, and closing the left atrial appendage.

BACKGROUND

The left atrial appendage (LAA) is a muscular pouch connected to the left atrium of a heart. Since the LAA lies within the confines of the pericardium and in close relation to the free wall of the left ventricle, its emptying and filling may be significantly affected by left ventricular function.

When patients have a normal heart rhythm, the atrial appendage squeezes rhythmically with the rest of the left atrium. In doing so, all of the blood in LAA is ejected into the left atrium and distributed all over the body, including the muscles, the organs, and the brain, with the rest of the blood from that chamber.

Atrial fibrillation is a common rhythm disturbance in older patients, in which the top chambers of the heart do not beat regularly. In a fibrillating atrium, the LAA becomes a major site of blood stasis, which significantly increases the risk of clot formation. Indeed, almost 15% of all patients with nonvalvular atrial fibrillation (NVAF) develop thrombus in their heart. For those who are at the highest risk for thromboembolic events, anticoagulation, including warfarin and the newer anticoagulants, has been offered. However, this is a difficult medication and patient compliance can be difficult. Dietary restrictions are necessary, the dose of the medication may need to be changed frequently, and blood testing is required at least once a month. In addition, anticoagulation increases the risk of both intracerebral and extracranial bleeding.

Approximately 30% to 50% of patients with atrial fibrillation are not even eligible to receive anticoagulation. In the recent years, several percutaneous LAA occlusion devices have been developed. The Percutaneous Left Atrial Appendage Transcatheter Occlusion (PLAATO) device (Appriva Medical) was the first to be tested and used in humans. Since then, multiple devices have emerged, including the Amplatzer device (AGA Medical Corporation/St. Jude Medical), the Watchman device (Boston Scientific), the WaveCrest device (Coherex), LAA occluder (Occlutech), and LAmbre device (Lifetech). A common characteristic of these devices is a relative large metal cage designed to self-expand and lodge into the LAA. It has been reported that a significant learning curve exists for physicians to adopt these treatments. Device-related embolization during or after the procedure and erosion of the device into the tissue are constant concerns for these implants LARIAT suture delivery device (SentreHeart) differs from all the above implant devices—only a suture is used to tie-up the LAA. The LARIAT device is deployed by a trans-pericardial approach, specifically, by using an epicardial snare with a pre-tied suture to lasso and occlude the LAA. Both the intracardiac trans-septal access to the LAA and direct pericardial access are required. There are many access-related complications associated with the LARIAT device, including serious pericardial effusion and major bleeding.

Surgical techniques to occlude the LAA also continue to evolve, with efforts being made to overcome the inconsistent closure, tissue tearing, and intrathoracic bleeding associated with suturing or stapling techniques. For example, a widely used device, the AtriClip® (Atricure), consisting of a parallel titanium crossbar clip covered with woven polyester fabric, has received a CE Mark and is approved by the FDA for the closure of the LAA under direct visualization in conjunction with other open cardiac surgical procedures.

Thus, drawbacks in each existing LAA closure device/method continue to demand improvement on the LAA closure technology, such as an effective closure without post-procedure complications, minimum use of metal in the implant, and minimum invasion approaches with less recovery time.

SUMMARY

One aspect of the present teachings provides a method for resizing a LAA chamber. The method comprises inserting a locating wire from the right atrium, across the atrial septum, across the left atrium, and into the LAA chamber. The method further comprises placing the locating wire across a tissue wall at a first location inside the LAA chamber and implanting a first tissue anchor at the first location. The method further comprises placing the locating wire across a tissue wall at a second location inside the LAA chamber, and implanting a second tissue anchor at the second location. By pulling the first and second tissue anchors toward each other, the tissue walls at the first and second locations of the LAA chamber are pulled together.

Another aspect of the present teachings provides a method for resizing a LAA chamber. The method comprises inserting a locating wire from the right atrium, across the atrial septum, across the left atrium, and into the LAA chamber. The method further comprises placing the locating wire across a tissue wall at a first location inside the LAA chamber, and implanting a first tissue anchor at the first location. The method further comprises placing the locating wire across the tissue wall at a second location inside the LAA chamber, and implanting a second tissue anchor at the second location. The method further comprises placing the locating wire across the tissue wall approximate to a bottom of the LAA chamber, and implanting a third tissue anchor at the third location. By pulling the first, second, and third tissue anchors toward one another, the bottom of the LAA chamber is everted, and the tissue walls at the first, second, and third locations of the LAA chamber are pulled together.

Another aspect of the present teachings provides a method for resizing a LAA chamber. The method comprises implanting a first tissue anchor at a first location across a tissue wall inside a LAA chamber. The method further comprises implanting a second tissue anchor at a second location across a tissue wall inside the LAA chamber. In one embodiment, the first tissue anchor is larger than the second tissue anchor. By pulling the first and second tissue anchors toward each other, the LAA chamber collapses.

Another aspect of the present teachings provides a method for resizing a LAA chamber. The method comprises implanting a first tissue anchor at a first location across a tissue wall inside a LAA chamber. The method further comprises implanting a second tissue anchor at a second location across a tissue wall inside the LAA chamber. The method further comprises filling the LAA chamber with a space-filling material. By pulling the first and second tissue anchors toward each other, the tissue walls at the first and second locations of the LAA chamber are pulled together, and the space-filling material is prevented from escaping the LAA chamber.

DETAILED DESCRIPTION

Figure 1:
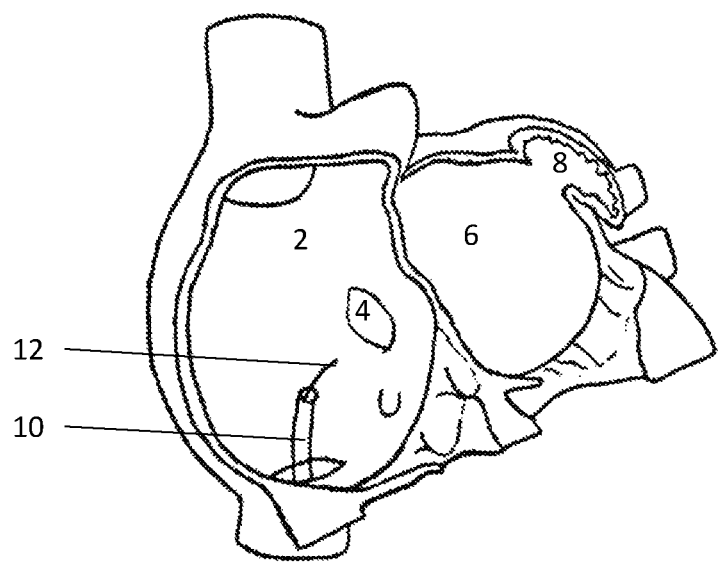
FIG. 1 is a perspective view of an embodiment of the present teachings where a locating wire is positioned inside the right atrium according to the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction relatively away from a catheter insertion location and "proximal" refers to the direction relatively close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and appended claims are approximations. At the very least and not as an attempt to limit the application of the doctrine of equivalents to the scope of the claims, numerical parameters should be read in light of the number of reported significant digits and the application of ordinary rounding techniques.

In one aspect, the present teachings relate to percutaneous treatment methods and systems that reduce the size of the LAA chamber (8) and/or close off the opening of the LAA. In various embodiments, the treatment system can also be used in conjunction with other LAA closure implants and materials. A person with ordinary skill in the art would recognize that the figures and description thereto refer to various embodiments of the present teachings and, unless indicated otherwise by their contexts, do not limit the scope of the attached claims.

An aspect of the present teachings relates to methods of creating a percutaneous access to the LAA via a transeptal approach. In various embodiments, the method includes locating a first implantation site along the LAA chamber wall (18) with a tissue piercing wire. In various embodiments, the first tissue anchor (20) is implanted at such location. In various embodiments, following the same methods, one or more than one tissue anchors (20) are then implanted at another or other locations along the LAA chamber wall (18). Once a clinician is satisfied with the secure implantation of the multiple tissue anchors (20), in some embodiments, she/he would then pull all the anchors toward one another. As the tissue anchors (20) coming closer to each other, the side wall of the LAA chamber (8) is drawn radially inward. Another aspect of the present teachings includes using a lock to secure the tensioned position of the tissue anchors (20), thereby completing the resizing and/or closure of the LAA chamber (8).

In one aspect of the present teachings, where the tissue anchors (20) are implanted near the opening of the LAA chamber (8), the opening of the LAA chamber (8) are closed off as the anchors are pulled together. In another aspect of the present teachings, where at least one tissue anchor (20) is implanted at the bottom of the LAA chamber (8) while the other anchors are implanted along the side wall of the LAA chamber (8), as the tissue anchors (20) are drawn toward one another, the bottom of the LAA chamber (8) is everted and the LAA chamber (8) is effectively eliminated.

In another aspect of the present teachings, a first tissue anchor (20) is implanted near the opening of the LAA chamber (8), and a second tissue anchor (30) greater in size than the first tissue anchor (20) is implanted opposite of the first anchor. As the two tissue anchors (20) are drawn toward each other, the LAA chamber wall (18) collapses. In one embodiment, the second tissue anchor (30) has a bar shaped deployed profile. In another embodiment, the second tissue has an expanded umbrella-shaped or plate-shaped deployed profile.

Another aspect of the present teachings provides a method for closing a LAA chamber (8) using the tissue anchor (20) system in combination with other treatment mechanisms. According to one embodiment, the LAA chamber (8) is first filled with a gel or other space filler, then closed with tissue anchors (20) as described herein.

In one aspect of the present teaching, at least one tissue anchor (20) is implanted along the LAA chamber wall (18) while within 2-4 mm to the junction of the LAA and atrium chamber. In another embodiment, for the umbrella-shaped, or plate-shaped tissue anchor (80) has a general diameter of 15-30 mm.

According to some embodiments of the present teachings, the treatment procedure starts with establishing a percutaneous access to LAA. FIG. 1 illustrates that a wire delivery catheter (10) assembly percutaneously reaches the right atrium (2). The wire delivery catheter (10) assembly includes a locating wire (12) and a wire delivery catheter (10). The wire delivery catheter (10) has a proximal end, a distal end, and a longitudinal lumen extending from its proximal end to its distal end. The locating wire (12) is slidably disposed within the longitudinal lumen of the wire delivery catheter (10). According to some embodiments, a distal portion of the wire delivery catheter (10) is configured to be able to articulate to various directions according to the anatomy in order for its distal end to be positioned nominal to the tissue.

The locating wire (12) also has a proximal end, a distal end configured for tissue piercing, and an elongated body extending from the distal end to the proximal end. In some embodiments, the distal end of the locating wire (12) has a sharpened profile for piercing through the heart tissue. In another embodiment, the distal end of the locating wire (12) is configured to connect to a RF energy source. In some embodiments, the locating wire (12) has a relatively flexible distal portion so that once inside the wire delivery catheter (10), the distal portion of the locating wire (12) straightens and adopts the profile of the distal portion of the catheter; and once outside of the wire delivery catheter (10), the distal portion of the locating wire (12) deflects and avoids accidentally puncture the heart wall.

According to some embodiments, a wire delivery catheter (10) assembly reaches the right atrium (2) of the heart via a standard right heart catheterization, that is, through the femoral vein, the inferior vena cava, and the right atrium (2). In various embodiments, the procedure includes transseptally accessing the left atrium (6) via a septal puncture.

Figure 2:
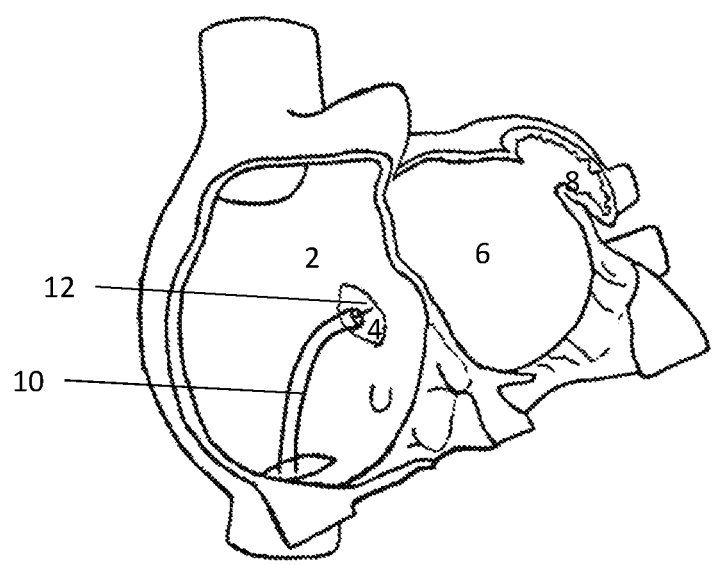
FIG. 2 is a perspective view of an embodiment of the present teachings where a locating wire transeptally accesses the left atrium according to the present teachings.

Once the distal end of the wire delivery catheter (10) assembly is inside the right atrium (2), a distal end of the wire delivery catheter (10) extends further distally. As shown in FIG. 2, the distal end of the wire delivery catheter (10) presses against the atrial septum. According to some embodiments, the distal end of the wire delivery catheter (10) positions against the fossa ovalis (4) and the wire (12) is then advanced distally to pierce the septum at the fossa ovalis (4). In one embodiment, the wire is designed to have a sharp distal tip that is configured to pierce the septum. In another embodiment, such trans-septal puncture is accomplished with the assistant of a radiofrequency energy.

The present teachings as described herein provides an embodiment where the access across the heart tissue is established with the wire delivery catheter (10) and the locating wire (12). In some embodiments, the wire delivery catheter (10) and the locating wire (12) are combined to establish the access across the heart tissue. In one embodiment, the distal end of the wire delivery catheter (10) is pressed against the atrial septum and the locating wire (12) is held close to the tissue surface. One skilled in the art should understand that such tissue piercing procedure could be accomplished by the locating wire (12) acting alone, or in combination with other appropriate design. The embodiments disclosed herein should not be viewed as limiting to the scope of the present teachings.

According to one embodiment of the present teachings, a guide catheter (14) tracks over the wire delivery catheter (10), crossing the atrial septum. The guide catheter (14) remains across the septum with its distal end extending inside the left atrium (6) throughout the entire procedure. In such way, an access path for all implants to be deployed and the delivery system carrying the implants are established. The guide catheter (14) has an elongated body with an axial lumen extending from a proximal end to a distal end. The proximal end of the catheter (14) remains under the control of a clinician throughout the procedure.

Figure 3:
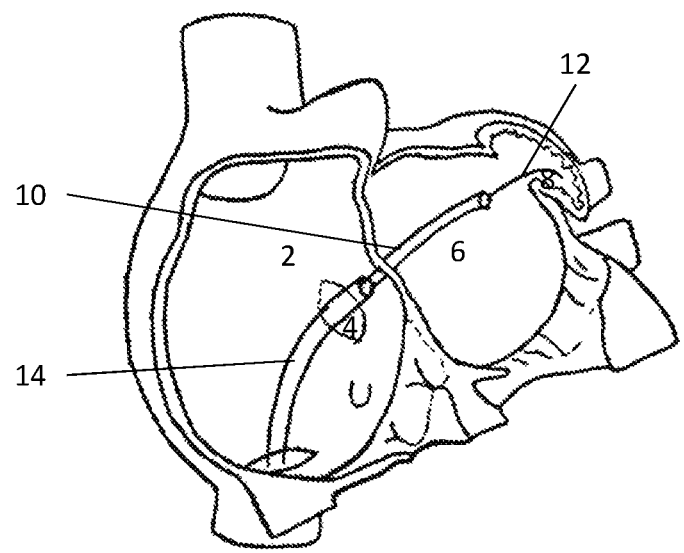
FIG. 3 is a perspective view of an embodiment of the present teachings where a distal end of a locating wire reaches the left atrial appendage in accordance with the present teachings.
Figure 4:
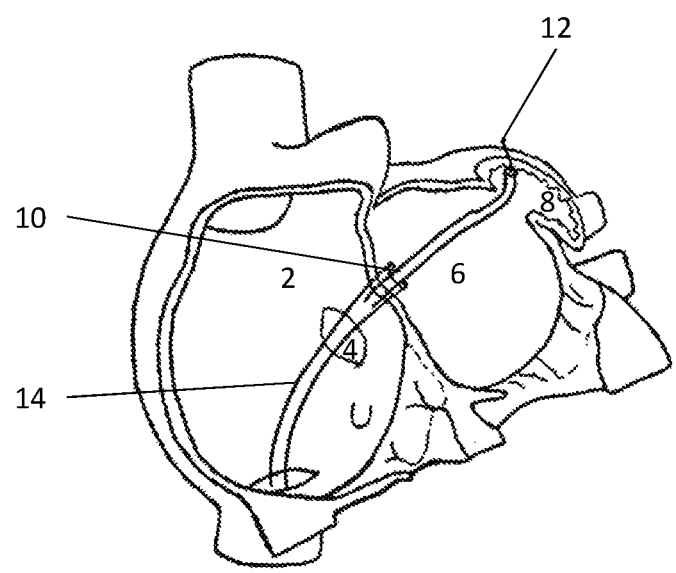
FIG. 4 is a perspective view of an embodiment of the present teachings where a wire delivery catheter tracking along a locating wire and the distal end of the wire delivery catheter reaches the left atrial appendage in accordance with the present teachings.

Continue referring to FIG. 3, upon crossing the septum, the distal end of the wire delivery catheter (10) assembly extends distally toward LAA. According to some embodiments, the wire delivery catheter (10) assembly is further used to mark the implantation location. As the wire delivery catheter (10) assembly extends further distally, its distal end reaches inside the LAA chamber (8). Once the distal end of the wire delivery catheter (10) is positioned inside the LAA chamber (8), the clinician actuates the distal portion of the wire delivery catheter (10) so that the distal end faces the inner wall of the LAA chamber (8), for example, as shown in FIG. 4. The locating wire (12) then further advances distally with its distal tip piercing the side wall of the LAA chamber (8) and marking the first implantation location.

One skilled in the art should appreciate that the wire delivery catheter (10) disclosed herein may have distal portions that are steerable in various manners for accurate positioning. For example, the distal end portion of the wire delivery catheter (10) is steerable into a desired hockey-curve or hook-like position by a guiding cable embedded in the luminal wall of the catheter, which may be pulled to configure the distal end portion of catheter into the hook-like shape as shown. In some embodiments, a catheter utilized herein includes a unidirectional or bi-directional steering mechanism. A steering mechanism may be positioned within and/or on the device. Typically, the steering mechanism may include a pull wire terminating at a flat spring or collar at the distal end of the wire delivery catheter (10). The steerable catheter has a more flexible distal section compared to the proximal portion of the catheter body. When tension is placed on the pull wire, the distal end of the catheter deflects into a curved or bend shape, which in turn guides the locating wire (12) to face accurately toward the tissue to be pierced at the intended location. The pull wire may be wound, crimped, spot welded, or soldered to the distal end of the wire delivery catheter (10). This provides a stable point within the wire delivery catheter (10) for the pull wire to exert a tensile force and steer the distal portion of the catheter. The more proximal portion of the catheter may be reinforced by incorporating a helically wound or braided wire therein to provide column support from which to better deflect the distal section.

Other steerable mechanisms should also work for the wire delivery catheter (10) disclosed herein. For example, the steering mechanism may consist of a body with a relatively flexible distal portion and a relatively rigid proximal portion; and a superelastic steering wire that is configured to slide in and out of a side lumen of the wire delivery catheter (10). The superplastic steering wire is pre-programmed to have a desired three-dimensional geometric shape for atrial septal puncturing as well as LAA chamber wall (18) piercing at its distal portion. Extending the preformed steering wire into the relatively flexible distal section of the wire delivery catheter (10) causes its distal section to assume the shape of the steering wire. Retracting the preformed steering wire proximally away from the relatively flexible distal portion, and back into the relatively rigid proximal section of the wire delivery catheter (10), the distal portion of the wire delivery catheter (10) straightens. Another example of the steerable catheter construct includes a pre-defined curve, for example, around 90°, preformed into the distal section, which allows the distal end of the wire delivery catheter (10) biases toward the tissue within an appropriate heart chamber. During a vascular delivery, such distal portion is then straightened by incorporating a tube or rod that can be advanced through that section. One skilled in the art should recognize what has been described here should only be viewed as examples, and not to limit the scope of the present teachings.

According to some embodiments, the locating wire (12) is coupled with a suitable RF energy device (not shown) where the distal tip of the locating wire (12) is configured to deliver radiofrequency (RF) energy to assist its crossing of the atrial septum, as well as the tissue wall of the LAA chamber (8). The distal tip of the locating wire (12) is designed to be atraumatic to prevent any inadvertent tissue damage. Once the distal tip is positioned approximately to the tissue to be pierced, the RF energy is activated to ablate the tissue within its range without contacting the tissue. Once the distal tip of the locating wire (12) crosses through the tissue, the RF energy is then deactivated. Alternatively, the locating wire (12) can have a piercing tip which allows it to perforate the atrial septum as well as the tissue wall of the LAA chamber (8). In such embodiments, the piercing tip is configured to be hidden during the delivery and actuated when facing the tissue to be crossed. The locating wire (12) can adopt many shapes and profiles for the purpose of this application, including, for example, the RF wire disclosed in U.S. patent application Ser. No. 14/138,926, filed on Feb. 26, 2013, entitled "ENERGY ASSISTED TISSUE PIERCING DEVICE AND METHOD OF USE THEREOF," each of which is incorporated herein by reference in its entirety. One skilled in the art should understand that other methods and devices can also be used to assist the piercing or traversing of the heart tissue. Thus, the particular examples described herein should not be viewed as limiting to the scope of the present teachings.

Figure 5:
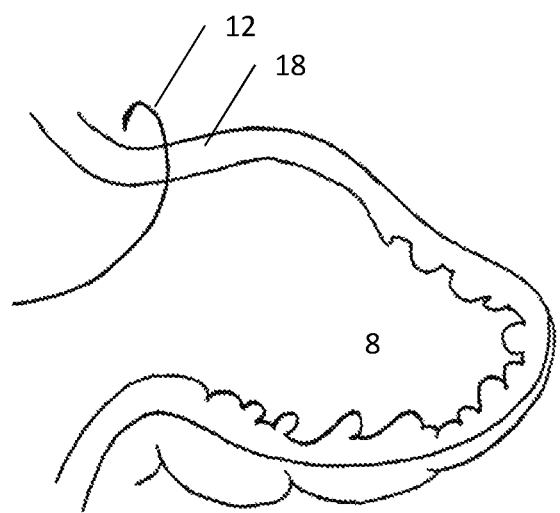
FIG. 5 is a perspective view of an embodiment of the present teachings where a locating wire pierces across the side tissue wall of the LAA camber at a first location in accordance with the present teachings.
Figure 6:
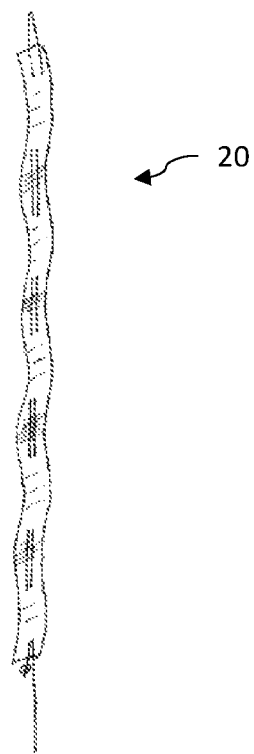
FIG. 6 is an embodiment of the tissue anchor in its delivery profile according to the present teachings.

Now referring to FIG. 5, the distal end of the locating wire (12) is placed across the LAA chamber wall (18) at a location within the LAA chamber (8) and near its opening, and a first tissue anchor is deployed at a location with the wire delivery catheter (10) removed out of the way. According to some embodiments, as illustrated in FIGS. 6-8, a tissue anchor delivery catheter (22) tracks along the locating wire (12) and across the LAA chamber wall (18). In certain embodiments, the tissue anchor delivery catheter (22) is used to deliver a tissue anchor (20) to the first implantation location inside the LAA chamber (8). In one embodiment, the wire delivery catheter (10) withdraw proximally first, and the tissue anchor delivery catheter (22) tracks along the locating wire (12), follows the delivery path maintained by the guide catheter (14), and reaches the first implantation location. One skilled in the art should understand that the tissue anchor delivery catheter (22) could track along the locating wire (12) by sliding over the proximal end of the locating wire (12), or alternatively the tissue anchor delivery catheter (22) could track along the locating wire (12) through a monorail fashion. Both embodiments should be viewed as within the scope of the present teachings.

Figure 7A:
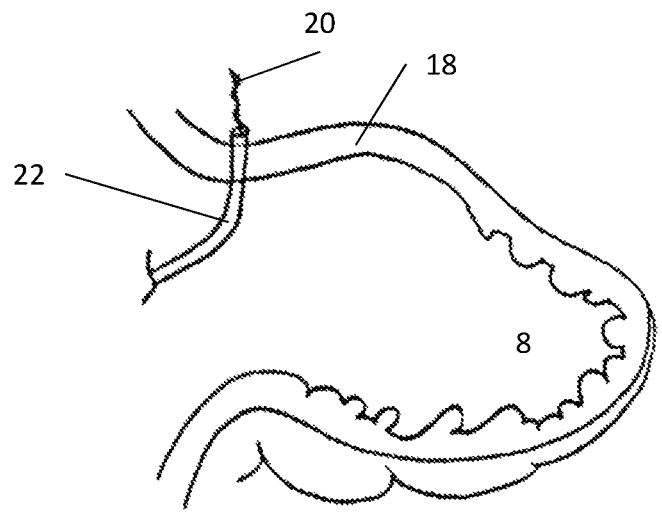
FIGS. 7A-7C is an embodiment of the deployment of a first tissue anchor according to the present teachings.
Figure 7B:
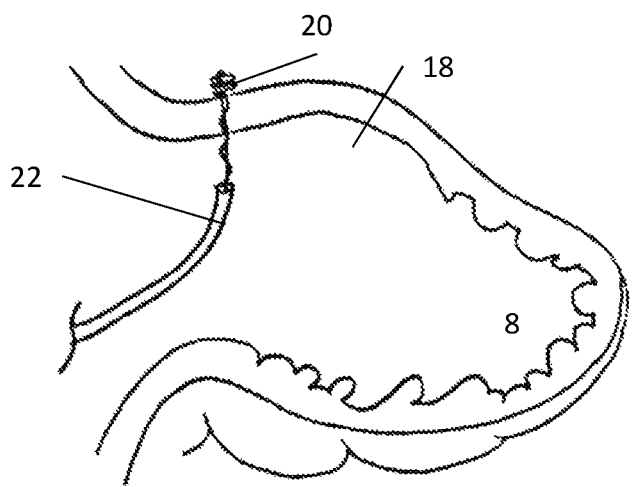
Figure 7C:
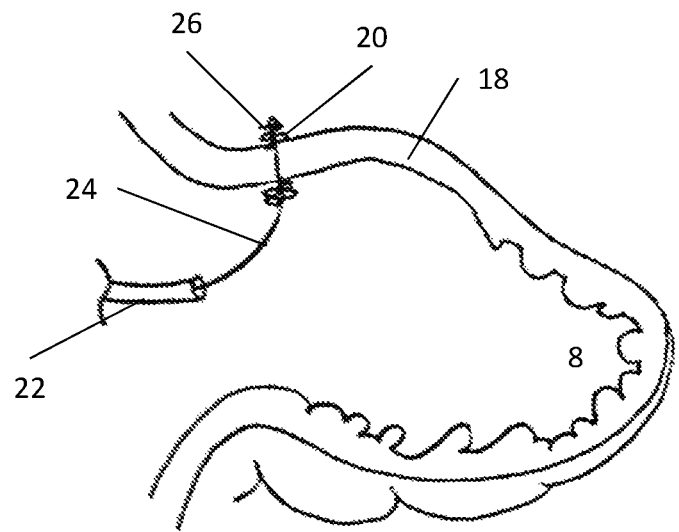
Figure 8:
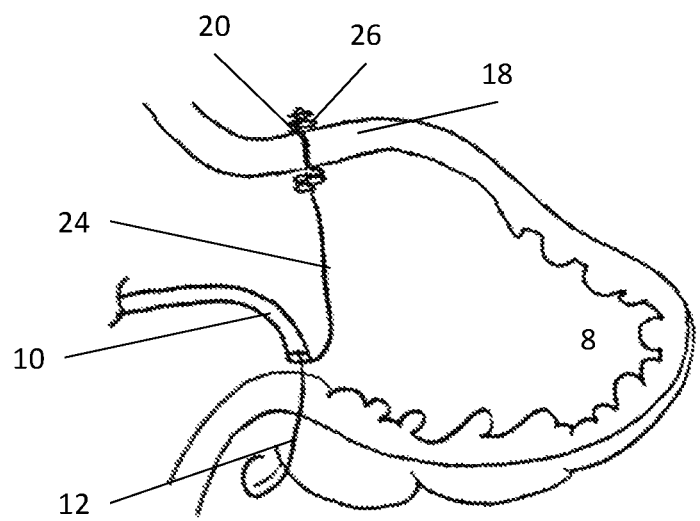
FIG. 8 is a perspective view of an embodiment of the present teachings where the locating wire pierces across the side tissue wall of the LAA camber at a second location in accordance with the present teachings.

FIGS. 7A-7C illustrate a first tissue anchor (20) deployed across an implantation site. One exemplary first tissue anchor (20) is shown in FIG. 6. According to some embodiments of the present teachings, the exemplary tissue anchor (20) includes an anchor element (26) and a tensioning member (24). As shown in FIG. 6, the anchor element (26) has a unitary configuration with a plurality of folded panels. The tissue anchor (26) is coupled to a tensioning member (24), in this example, a suture, by threading the suture distally through the anchor element (26) and proximally through the anchor element (26). A slip knot or another type of locking mechanism is formed so that when a proximal end portion of the tensioning member (24) is pulled, all of the anchor element (26) are drawn together to form a plurality of panels along the pre-set folding lines. In addition, the pulling of a proximal end portion of the tensioning member (24), in some embodiments, draws the anchor element (26) at the distal end first and those at the proximal end next, as discussed elsewhere herein. Accordingly, in various embodiments, a tissue anchor (20) of the present teachings has a delivery profile where all panels are unfolded and elongated, and a deployed profile where all panels are folded, preferably along the pre-set folding lines, thereby shortening its longitudinal profile. According to some embodiments, the anchor element (26) is made from a surgical grade fabric material (e.g., a polyester material such as DACRON). In some embodiments, the anchor element (26) is designed to promote tissue in-growth so that the anchors become at least in part encased in tissues over-time.

Accordingly, in various embodiments, a tissue anchor (20) of the present teachings includes an elongate or delivery configuration and a shortened or deployed configuration. In some embodiments, in the deployed configuration, the anchor elements (26) are folded and is attached to a long "tail" of the tensioning member (24), for example, a suture, leading from the anchor, for example, as shown in FIGS. 7A-7C. In some embodiments, the long "tail" can be used for attaching additional tissue anchors (20), tensioning, and plication, as described herein.

FIGS. 7A-7C illustrate an exemplary delivery and deployment of a first tissue anchor (20) across the LAA chamber wall (18). FIG. 7A illustrates the process of exposing the distal portion of the tissue anchor (20) and FIG. 7B illustrates the process of exposing the proximal portion of the tissue anchor (20). FIG. 7C illustrates an exemplary deployed tissue anchor (20) positioned at the location.

Once the locating wire (12) is placed at a first location across the LAA chamber wall (18), the wire delivery catheter (10) is withdrawn proximally from the body, leaving the wire to mark the spot. Referring to FIG. 7A, in some embodiments, a tissue anchor delivery catheter (22) holding a tissue anchor (20) inside its longitudinal lumen tracks along the locating wire (12) and crosses the LAA chamber wall (18). Continuing referring to FIG. 7A, in some embodiments, the tissue anchor (20) is partially pushed distally outside of the distal end of the tissue anchor delivery catheter (22). Once the distal portion of the tissue anchor (20) or a sufficient amount of the anchor element (26) is exposed outside of the LAA chamber (8), a clinician can pull on the proximal end of the tensioning member (24) and cinch the exposed anchor element (26). The tissue anchor delivery catheter (22) is then retracted proximally so that the distal end of the tissue anchor delivery catheter (22) moves proximally and back inside the LAA chamber (8). The clinician then exposes the proximal portion of the tissue anchor (20) or the remainder of the anchor element (26) of the tissue anchor (20) within the right atrium (2) by further retracting the tissue anchor delivery catheter (22) proximally as shown in FIG. 7B. As the clinician pulls the proximal end of the tensioning member (24), the proximal portion of the tissue anchor (20) element is cinched.

As illustrated in FIG. 7C, in various embodiments, as the clinician pulls the proximal end of the tensioning member (24), the anchor elements (26) of the tissue anchor (20) are drawn together against the opposite sides of the LAA chamber (8), thereby securing the first tissue anchor (20) to the LAA chamber wall (18). As a result, as illustrated in FIG. 7C, in some embodiments, the first tissue anchor (20) is deployed across the LAA chamber wall (18) near the LAA opening at the first location with the distal portion of the tissue anchor (20) placed against the outside of the LAA chamber (8), the proximal portion of the tissue anchor (20) placed against the inside of the LAA chamber wall (18), and the tensioning member (24) of the first tissue anchor (20) extending proximally through the lumen of the tissue anchor delivery catheter (22) to the outside of the body. According to some embodiments, the locating wire (12) that marks the first location and maintains the tissue access during the deployment of the first tissue anchor (20) is withdrawn proximally after the distal portion of the tissue anchor delivery catheter (22) crosses the LAA chamber wall (18). In other embodiments, the locating wire (12) that marks the first location and maintains the annulus access during the deployment of the first tissue anchor (20) is withdrawn proximally after the entire tissue anchor (20) is deployed across the LAA chamber wall (18). According to some embodiments, upon withdrawn from the first implantation location, the distal end of the locating wire (12) retracts back inside the tissue anchor delivery catheter (22). In another embodiment, as the locating wire (12) retracts proximally from the first implantation location, it disengages the tissue anchor delivery catheter (22), and the distal end of the locating wire (12) remains inside the left atrium (6) during the deployment of the first tissue anchor (20). According to some embodiments, upon deployment of the tissue anchor (20) across the LAA chamber wall (18), the proximal end of the tensioning member (24) is controlled by the clinician from outside of the body.

FIGS. 6-7C are only one embodiment of the possible tissue anchor (20) to be implanted across the tissue. Many other shapes and profiles could be adopted for the purpose of this application, including, for example, the annulus anchors disclosed in U.S. Pat. No. 8,951,285, filed on Jul. 5, 2005, entitled "Tissue anchor and Anchoring System;" U.S. Pat. No. 8,951,286, filed on Nov. 19, 2008, entitled "Tissue anchor, Anchoring System and Methods of Using the Same;" U.S. patent application Ser. No. 14/581,264, filed on Dec. 23, 2014, entitled "Tissue anchor and Anchoring System;" U.S. Pat. No. 9,259,218, filed on Feb. 26, 2013, entitled "Tissue anchor and Anchoring System;" and U.S. Pat. No. 8,945,211, filed on Sep. 11, 2009, entitled "TISSUE PLICATION DEVICE AND METHOD OF ITS USE;" each of which is incorporated herein by reference in its entirety. One skilled in the art should also understand that examples of suitable tissue anchors include, but not be limited to, tissue fasteners, tissue pledgets, or tissue staples etc.

With the first tissue anchor (20) securely deployed at the first location across the LAA chamber wall (18), the clinician can deploy a second tissue anchor (30) at a second location according to some embodiments of the present teachings. FIGS. 8-9C illustrate an exemplary deployment of a second tissue anchor (30) at a second location across the LAA chamber (8).

According to some embodiments, similar to what is described herein, for example, in FIGS. 7A-7C, a clinician uses the similar steps to position the wire delivery catheter (10) against the LAA chamber wall (18) from inside the LAA chamber (8) at a second location. According to some embodiments, once the first tissue anchor (20) is securely deployed, the tissue anchor delivery catheter (22) is withdrawn from the body, leaving a tensioning member (24) with one end connecting to the tissue anchor (20) and the other end outside of the body and remaining under the control of the clinician. A clinician extends the wire delivery catheter (10) sliding over the location wire that remains inside the left atrium (6) until the distal end of the wire delivery assembly enters the LAA chamber (8) and remains in place. The distal end of the wire delivery catheter (10) is placed against the LAA chamber wall (18) by using similar methods described herein or known to those with ordinary skill in the art.

Similar to what is described herein in accordance with FIGS. 7A-7C, one end of the locating wire (12) is advanced across the LAA chamber wall (18) as illustrated in FIG. 8. As illustrated in FIG. 8, it results in that the locating wire (12) is placed at the second location with the distal end of the wire outside of the LAA chamber (8).

Figure 9A:
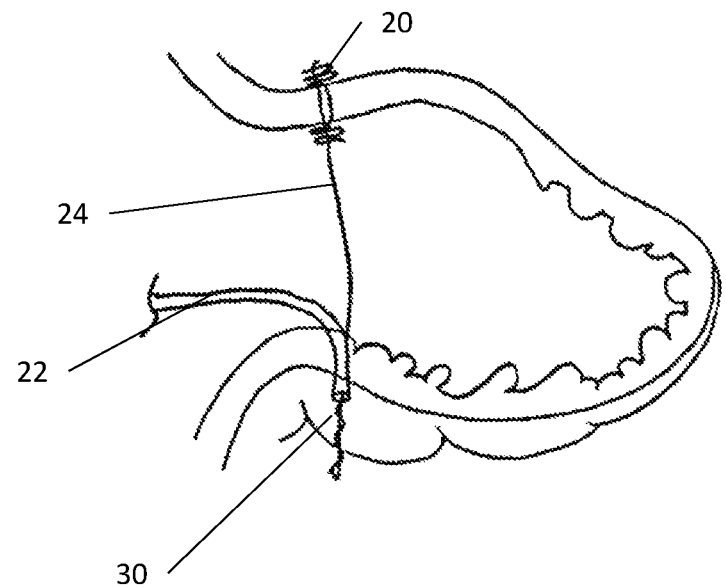
FIGS. 9A-9C is an embodiment of the deployment of a second tissue anchor according to the present teachings.
Figure 9B:
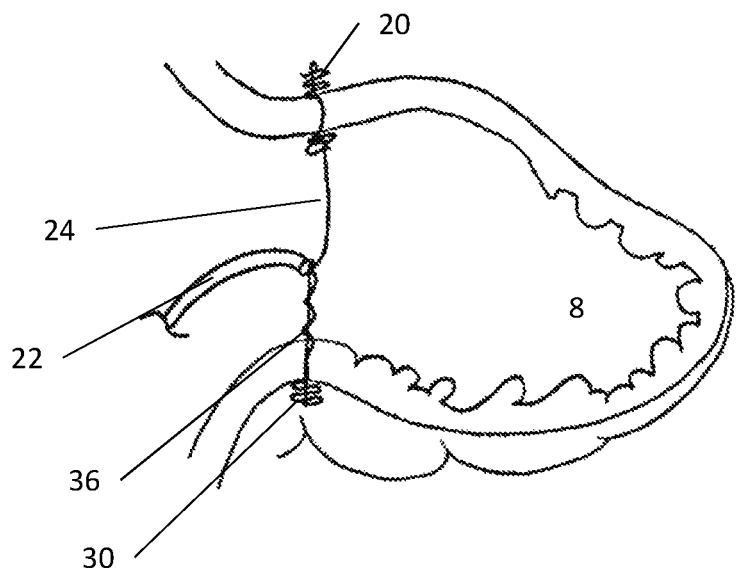
Figure 9C:
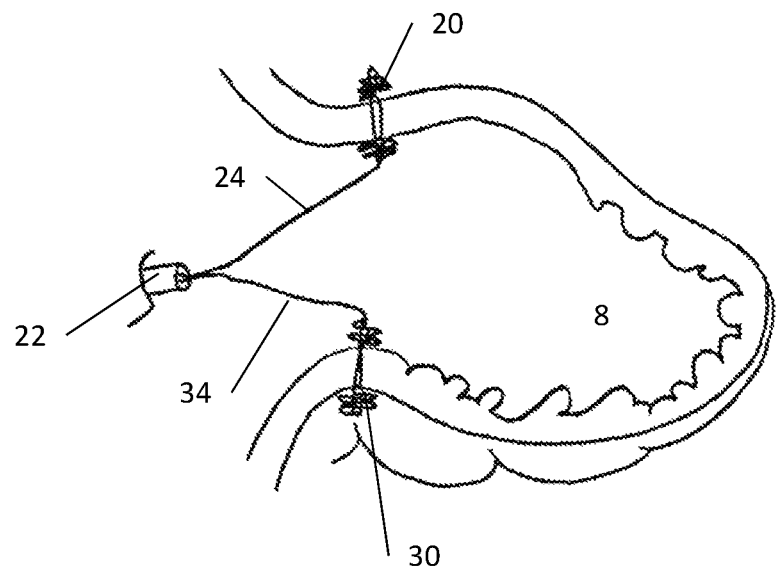

In various embodiments, a second tissue anchor (30) is deployed at the second location according to various embodiments described herein and as shown in FIGS. 9A-9C. FIGS. 9A-9C illustrate the embodiments where the second tissue anchor (30) is deployed across the LAA chamber (8) at the second location with the distal portion of the second tissue anchor (30) placed against the outside of the LAA, the proximal portion of the tissue anchor (30) placed against the inner LAA chamber wall (18), and the tensioning member (34) of the second tissue anchor (30) extending proximally through the trans-septal access to the outside of the body. Similar to what have been described above, during the deployment of the second tissue anchor (30), the locating wire (12) is withdrawn proximally with the distal end of the locating wire (12) either remaining inside the tissue anchor delivery catheter (22) or disengaging the tissue anchor delivery catheter (22) and remaining inside the left atrium (6).

As illustrated in FIG. 9C, two tissue anchors (20, 30) are implanted across the LAA chamber wall (18) near the opening. According to some embodiments, such as shown in FIG. 9C, each tensioning member (24, 34) connects a tissue anchor (20, 30), and the two tissue anchors (20, 30) are spaced apart along the circumference of the LAA chamber (8). According to some embodiments of the present teachings, two tissue anchors (20, 30) are sufficient for closing the opening of the LAA. Yet in other embodiments, more than two tissue anchors are needed to completely close a LAA opening. One skilled in the art should understand that the number of tissue anchors needed for closing a LAA chamber (8) should be decided by a clinician and based on each patient's anatomy and treatment plan. Exemplary embodiments shown and described herein should not be viewed as limiting to the scope of the present teaching.

Once a sufficient number of tissue anchors are implanted along the LAA chamber wall (18), the tissue anchor delivery catheter (22) and the locating wire (12) can be removed from the body entirely. And a lock delivery assembly with a lock delivery catheter and a locker (38) can be extended distally through the access path maintained by the guide catheter (14), track over the tensioning member (24), and reach inside the LAA chamber (8).

Figure 10:
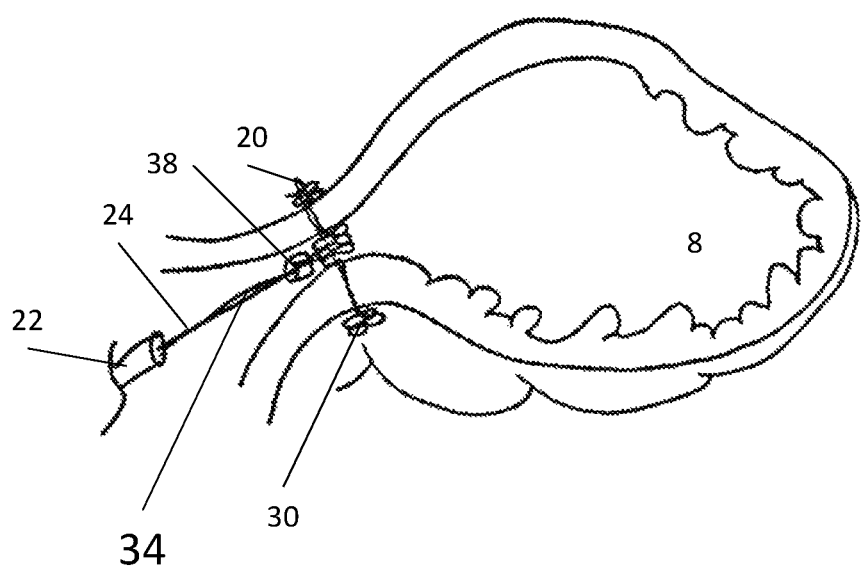
FIG. 10 is a perspective view of an embodiment of the present teachings where the first and second tissue anchors are pulled together and locked in place according to the present teachings.

FIG. 10 illustrates an exemplary closure of the opening of the LAA chamber (8). In various embodiments, the closure is achieved by applying tension to the two or more tissue anchors (20). In various embodiments, a clinician applies tension to the proximal end of the tensioning members (24). In some embodiments, this tension pulls the plurality of tissue anchors (20) closer to one another, thereby pulling the LAA chamber walls (18) toward one another and closing the opening. In some embodiments, this tension and the reduction of the circumference of the LAA are maintained, for example, by a locker or other locking mechanisms as shown in FIG. 10.

Suitable lockers include those well known in the art and those described in U.S. application Ser. No. 11/753,921, filed on May 25, 2007, entitled "Lockers for Surgical Tensile Members and Methods of Using the Same to Secure Surgical Tensile Members," the disclosure of which is incorporated herein by reference. With the tensioning members secured by a locker (not shown), the excess tensioning member proximal to the locker can be removed by a cutter, including, for example, a cutter disclosed in U.S. Pat. No. 8,911,461, filed on Nov. 5, 2007, entitled "Suture Cutter and Method of Cutting Suture," the disclosure of which is incorporated herein by reference.

Figure 11A:
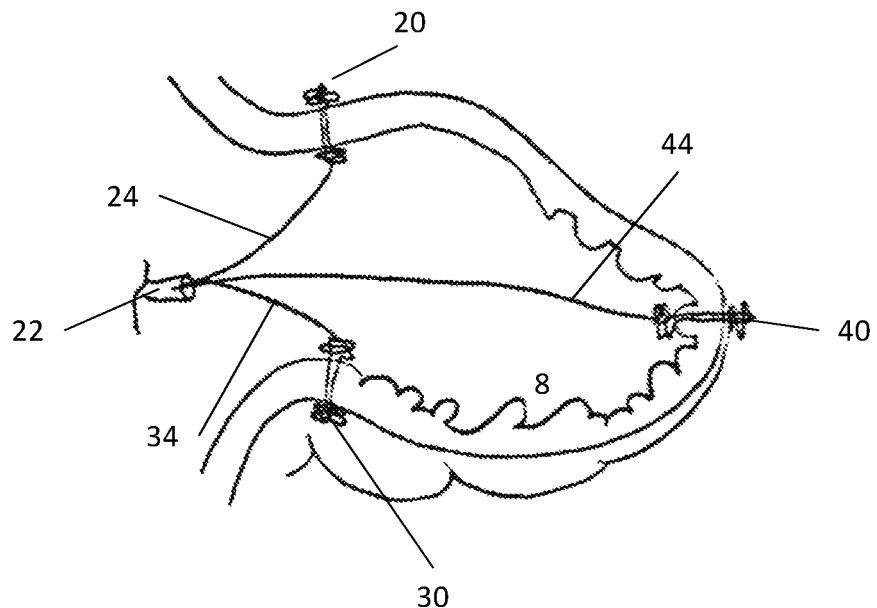
FIG. 11A is another perspective view of an embodiment of the present teachings where three tissue anchors are deployed at three different locations inside the LAA chamber according to the present teachings.
Figure 11B:
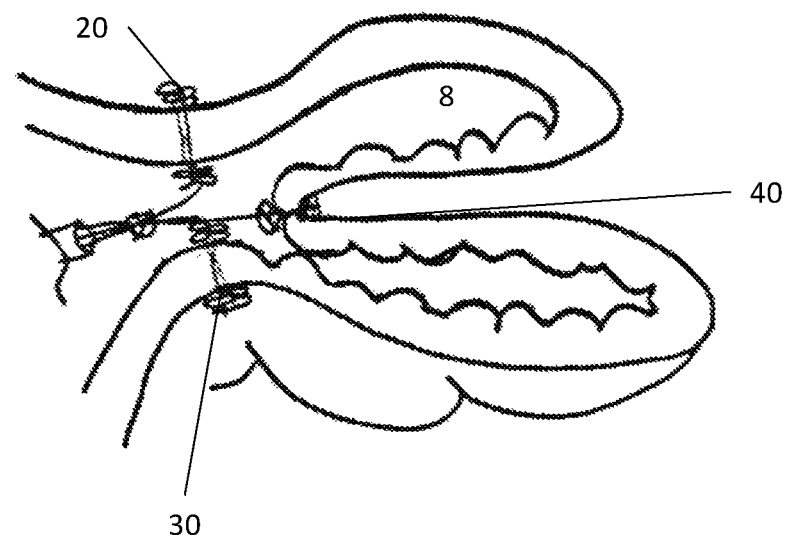
FIG. 11B is a perspective view of an embodiment of the present teachings where the three tissue anchors are pulled together and locked in place according to the present teachings.

According to some embodiments of the present teachings, such as shown in FIG. 10, two similar tissue anchors are implanted inside and across the LAA chamber wall (18) and at a similar distance to the LAA opening. And the implantation location can have various distances toward the LAA opening so long as the tissue anchors can achieve the intended closure. FIG. 11A illustrates another embodiment of the present teachings, where one tissue anchor (40) is implanted at the deep end of the LAA chamber (8), and two tissue anchors (20, 30) are implanted inside the LAA chamber (8) and across the tissue wall near the opening. Each tissue anchor (20, 30, & 40) is attached with a tensioning member (24, 34,& 44) and all the three tensioning members (24, 34, & 44) extend proximally from the respective tissue anchors (20, 30, & 40), across the left atrium (6), and back outside the body, and the proximal ends of the tensioning members remain under the control of a clinician. As illustrated in FIG. 11B, upon the clinician pulling on all three tensioning members (24, 34, & 44), the bottom of the LAA chamber (8) everts as the tissue anchor (40) at the deep end is drawn close to the other two tissue anchors (20, 30) near the opening of the LAA chamber (8). As all the three tissue anchors (20, 30, & 40) are drawn together, the LAA chamber (8) is effectively eliminated completely.

Although the embodiments in FIGS. 7 and 11 show three tissue anchors (20, 30, & 40) with a similar size are used to close and/or eliminate the LAA chamber (8), one skilled in the art should understand that, tissue anchors with various sizes could be used for the closure. Additionally, although the embodiments in FIGS. 9-11 show that two and/or three tissue anchors are used, one skilled in the art should understand that more or less than three tissue anchors could be used.

Figure 12A:
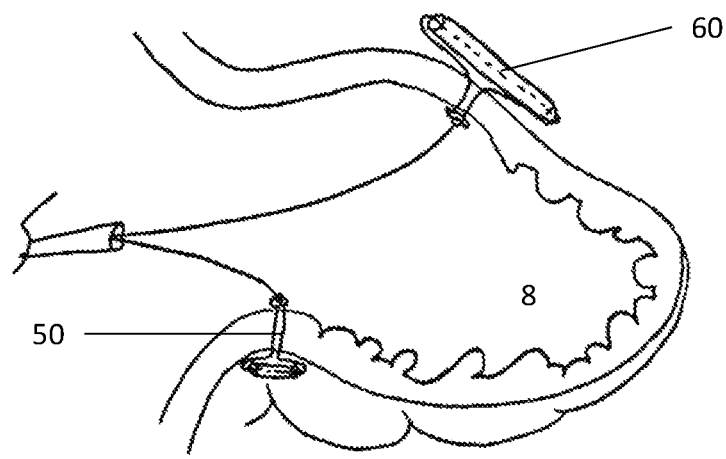
FIG. 12A is another perspective view of an embodiment of the present teachings where two tissue anchors of different sizes are deployed at two different locations inside the LAA chamber according to the present teachings.
Figure 12B:
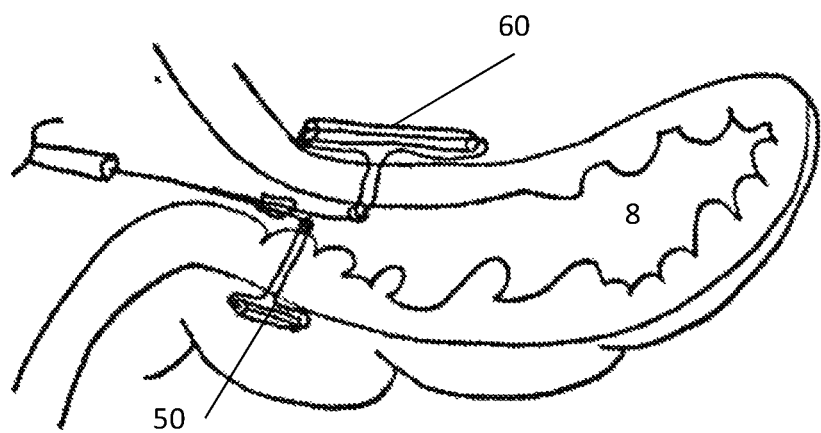
FIG. 12B is another perspective view of an embodiment of the present teachings where the two tissue anchors are pulled together and locked in place according to the present teachings.

According to another aspect of the embodiments, tissue anchors of more than one size are incorporated to close a LAA chamber (8). FIGS. 12A-12B illustrate another embodiment of the present teachings, where one smaller tissue anchor (50) similar to what has been described in U.S. Pat. No. 8,945,211, filed on Sep. 11, 2009, entitled "TISSUE PLICATION DEVICE AND METHOD OF ITS USE," is implanted across the tissue inside the LAA chamber (8) near the opening, and a larger second tissue anchor (60) is implanted at a second chamber wall location further away from the opening. As shown in FIG. 12A, the second tissue anchor (60) has an enlarged distal portion placed against outside of the LAA chamber wall (18). The proximal portion of the second tissue anchor (60) is placed against the inner wall of the LAA chamber (8). The size of the proximal portion of the second tissue anchor (60) can be as big as or bigger than its distal portion. The size of the proximal portion of the second tissue anchor (60) can also be smaller than its distal portion, for example, as illustrated in FIG. 12A. As the first and second tissue anchors (50, 60) are pulled together, the larger proximal portion of the second tissue anchor (60) pushes against the LAA chamber wall (18) and effectively causes the wall to collapse toward the opposite wall of the LAA chamber (8), thereby reducing, closing, and/or eliminating the LAA chamber (8), as shown in FIG. 12B. Although FIGS. 12A-12B illustrate one exemplary second tissue anchor, one skilled in the art should understand that other tissue anchor designs can be used for this purpose, and thus specific example disclosed herein should not be viewed as limiting to the scope of the present teachings.

Figure 13:
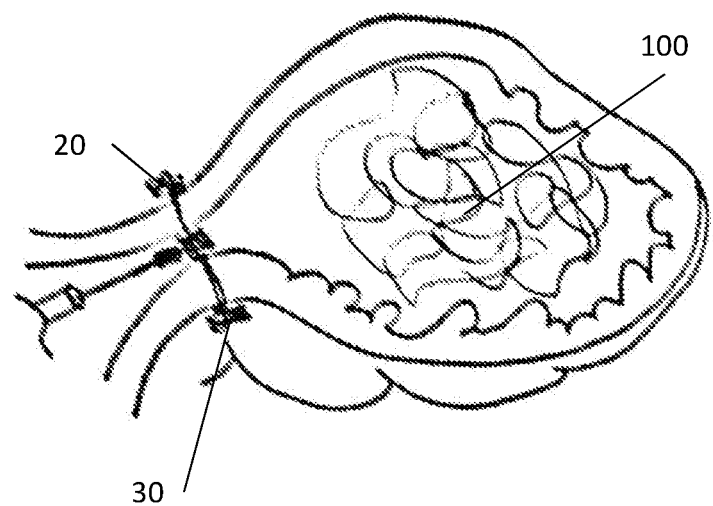
FIG. 13 is another perspective view of an embodiment of the present teachings where the LAA is filled with a space filling material and is closed off with two exemplary tissue anchors according to the present teachings.

According to some embodiments of the present teachings, the LAA closure system can also be used in addition to other treatment mechanisms. For example, FIG. 13 illustrates another embodiment of the present teachings, wherein a substantial portion of the LAA chamber (8) is filled with a space filling material (100). The opening of the LAA chamber (8) is then closed off with multiple tissue anchors (20, 30) implanted across the LAA chamber wall (18) near its opening, drawn to one another, and locked in place with a lock member. According to some embodiments, the filling material (100) could be a solid, a liquid, a gas, a foam, or a gel. The filling material (100) may include a saline solution or silicone. The filling material (100) may include a radiopaque material. The filling material (100) may include at least one bio-inert material or biocompatible material. The filling material (100) may include a first reagent and a second reagent, the second reagent being functional to activate the first reagent. It should be understood that other filling material (100) known to those skilled in the art could all be applicable here.

Figure 14:
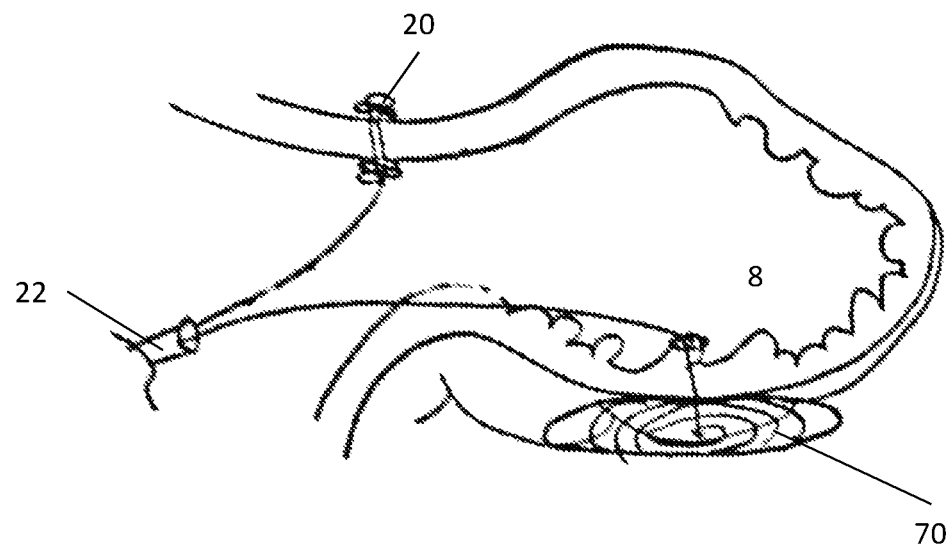
FIG. 14 is another perspective view of an embodiment of the present teachings where an exemplary closure plate is implanted inside the LAA chamber and the LAA is closed with two exemplary tissue anchors according to the present teachings.

FIG. 14 illustrates another embodiment, where the LAA closure system includes a first relatively smaller tissue anchor (20) and a second relatively large plate shaped tissue anchor (70) deployed opposite of the first smaller tissue anchor (20). In one embodiment, the first relatively smaller tissue anchor (20) is similar to the anchors described herein. In another embodiment, the second relatively larger tissue anchor (70) has a collapsed delivery profile and a radially expanded deployed configuration. At its delivery profile, the second tissue anchor (70) elongates and is housed inside the lumen of the tissue anchor delivery catheter (22). At its deployed profile, the second tissue anchor (70) expands radially and assumes a pre-defined open umbrella or plate like shape. FIG. 14 illustrates a closure plate positioned against outside of the LAA chamber (8), located somewhere half-way of the chamber length. Once the second tissue anchor (70) is pulled toward the first tissue anchor (20), the plate shape collapses a greater area of the LAA chamber wall (18) which ensures an enhanced closure.

Figure 15A:
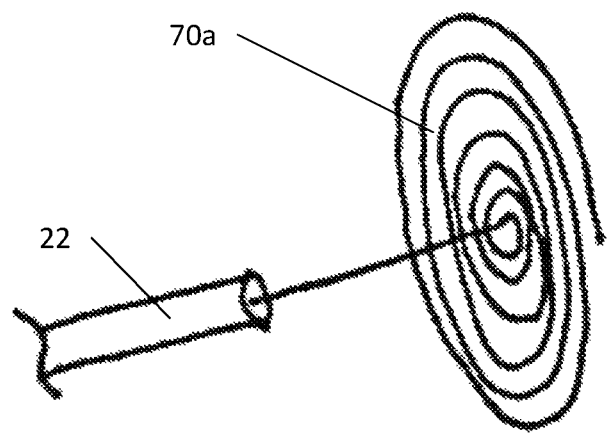
FIGS. 15A-15B are two exemplary embodiments of the deployed tissue anchor according to the present teaching.
Figure 15B:
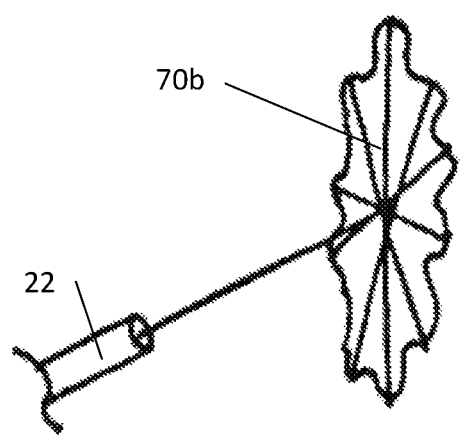

FIG. 15A-B illustrate some embodiments of second tissue anchor (70a) as described in FIG. 14, according to some embodiments of the present teachings. FIG. 15A illustrates one embodiment, where the deployed second tissue anchor (70a) is made of a continuous wire with spiral turns. The wire is straightened and housed inside the tissue anchor delivery catheter (22) during delivery. Once extending outside the catheter, the wire resumes its pre-defined shape, such as the one illustrated in FIG. 15A. FIG. 15B illustrates another embodiment, where the deployed second tissue anchor (70b) is made of multiple struts extending from a common center. The struts fold distally and radially inward while housed inside the tissue anchor delivery catheter (22) during delivery. Once the anchor extends outside of the catheter, the struts expand radially forming a plate/disc profile such as the one illustrated in FIG. 15b. FIGS. 15A-15B are two embodiments of the second large tissue anchor (70) as illustrated in FIG. 14. One skilled in the art should understand other tissue anchor designs could be adopted to achieve the same LAA closure purpose. Thus, the two embodiments provided herein should not be viewed as limiting to the scope of the present teaching.

One skilled in the art should understand that the LAA closure system described herein can also be used in combination with other treatment systems. The examples described herein should not be viewed as limiting to the scope of the present teaching.

Figure 16A:
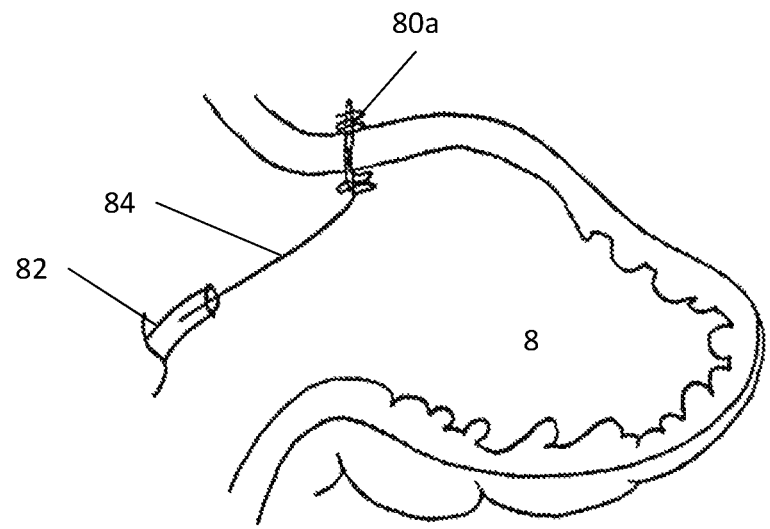
FIGS. 16A-16C are another embodiment of the deployment of a plurality of tissue anchors joined by one tensioning member according to the present teachings.
Figure 16B:
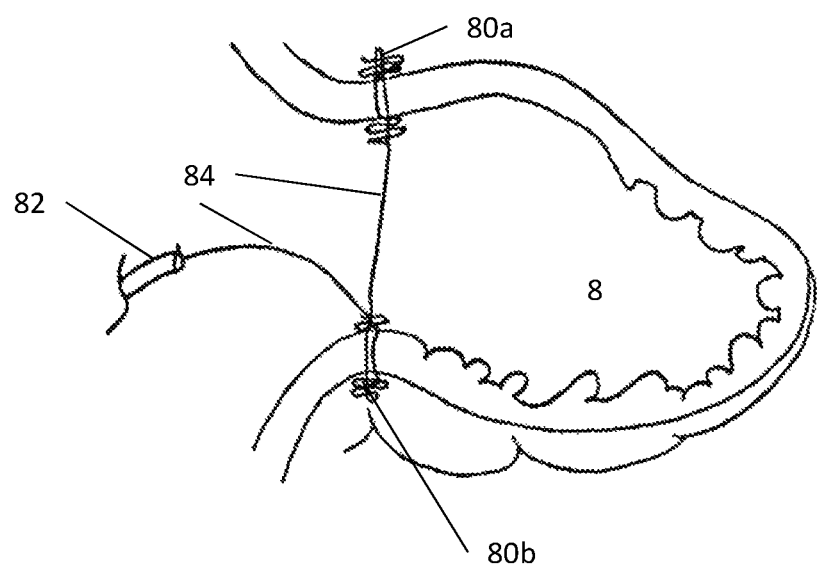
Figure 16C:
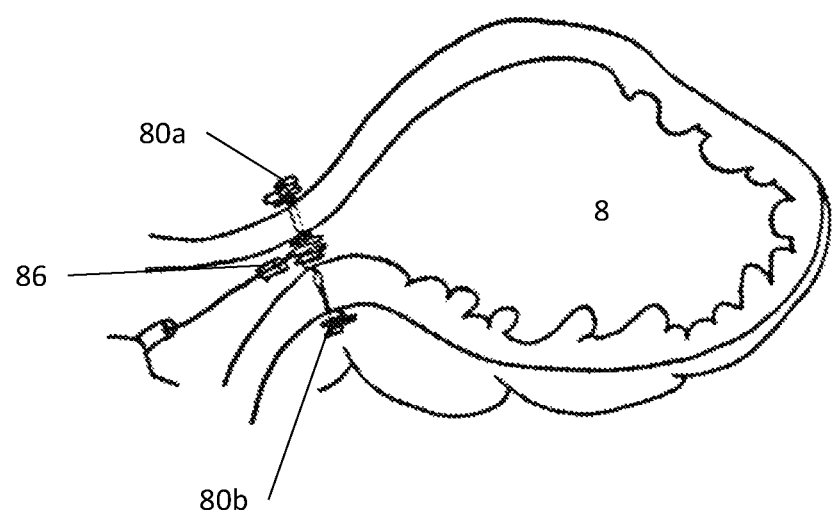

FIGS. 7-14 show that multiple tissue anchors, each of which connects to a tensioning member, and all the tensioning members are locked with a locker to secure the tensioned position among the anchors. One skilled in the art would understand that these tissue anchors can be connected with one tensioning member. In this case, by tensioning the one tensioning member, all three tissue anchors are drawn closer and the LAA is closed. FIGS. 16A-C illustrate another embodiment of the present teachings, where multiple tissue anchors (80a, 80b) are joined with one tensioning member (84). For example, the catheter can have two lumens arranged side by side, one for the locating wire, and the other for the tissue anchor. The distal end of the catheter is actuated to be positioned against the LAA chamber wall at a first location, so that the lumen of its distal portion is generally perpendicular to the tissue. The locating wire then pierces the tissue with its distal end crossing the tissue and reaching the outside of the LAA. A first tissue anchor (80a) follows the path created by the location wire, and deploys at the first location, as illustrated in FIG. 16A. Once the first tissue anchor (80a) is satisfactorily deployed at the first location, the locating wire is withdrawn proximally. The catheter is then actuated to be positioned at a second location inside the LAA chamber (8). The above described steps then repeat so that a second tissue anchor (80b) is implanted at a second location as illustrated in FIG. 16B. FIG. 16B further illustrates that all the tissue anchor (80a, 80b) are satisfactorily deployed in place, one tensioning member (84) having its distal end abutting one side of the first tissue anchor (80a), extending through the first tissue and anchor, continuing its way through the second tissue anchor (80b). The remaining portion of the tensioning member (84) extends through the tissue anchor delivery catheter (82) proximally to the outside of the body and remains under the control of a clinician. Upon the clinician pulling the tensioning member (24), the first tissue anchor (80a) is drawn closer to the second tissue anchor (80b) and the second tissue drawn closer to the third tissue anchor (not shown). A lock member (86) then secures all the three tissue anchors. As shown in FIG. 16C, the opening of the LAA chamber (8) is then closed. The multiple tissue anchors joined by one tensioning member also include those disclosed in U.S. patent application Ser. No. 14/662,203, filed on Mar. 18, 2015, entitled "TISSUE ANCHORS AND PERCUTANEOUS TRICUSPID VALVE REPAIR USING A TISSUE ANCHOR," the entirety of which is incorporated here by reference.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A method for resizing a left atrium appendage comprising,
   inserting a locating wire from a right atrium, across an atrial septum, across a left atrium, and into a left atrial appendage (LAA) chamber,
   advancing the locating wire through a tissue wall at a first location inside the LAA chamber,
   subsequently, implanting a first tissue anchor at the first location by advancing the first tissue anchor along the locating wire and into the tissue wall at the first location,
   subsequently, and independently of advancing the locating wire through the tissue wall at the first location, advancing the locating wire through the tissue wall at a second location inside the LAA chamber, subsequently, implanting a second tissue anchor at the second location by advancing the second tissue anchor along the locating wire and into the tissue wall at the second location, and subsequently, pulling the first and second tissue anchors toward each other so that the first and second locations of the LAA chamber are pulled together.

2. The method of claim 1, further including the steps of:

advancing the locating wire through the tissue wall at a third location approximate to a bottom of the LAA chamber, and subsequently, implanting a third tissue anchor at the third location by advancing the third tissue anchor along the locating wire and into the tissue wall at the second location, wherein pulling the first and second tissue anchors toward each other comprises pulling the first, second and third tissue anchors toward each other so that the bottom of the LAA chamber is everted and tissue wall at the first, second and third locations of the LAA chamber are pulled together.

3. The method of claim 1, wherein a distal end of the locating wire is configured to connect to an RF energy source, and wherein advancing the locating wire through the tissue wall at the first location comprises using the RF energy source to drive the distal end of the locating wire to apply RF energy to the tissue wall at the first location.

4. The method of claim 1, wherein advancing the first tissue anchor along the locating wire and into the tissue wall at the first location comprises advancing the first tissue anchor using a tissue anchor delivery catheter that tracks along the locating wire.

5. The method of claim 1, wherein:

the first tissue anchor has a unitary construction defined by a plurality of folded panels, the tissue anchor being coupled to a tensioning member that is threaded through the tissue anchor in a distal direction and is threaded through the tissue anchor in a proximal direction, and the method further comprises, subsequently to advancing the first tissue anchor along the locating wire and into the tissue wall at the first location, pulling a proximal end portion of the tensioning member such that the first tissue anchor becomes compressed to form the plurality of panels along pre-defined fold lines.

6. The method of claim 5, wherein the proximal end portion of the tensioning member extends outside the body, the tensioning member and the locating wire being disposed within a lumen of a common catheter.

7. The method of claim 1, wherein each of the first and second tissue anchors comprises a foldable anchor that has a tensioning member extending along a length thereof and the step of pulling the first and second tissue anchors toward each other comprises the step of pulling the tensioning members of the first and second tissue anchors.

8. The method of claim 7, further including, subsequently to pulling the tensioning members of the first and second tissue anchors, locking a lock member to the tensioning members of the first and second tissue anchors.

9. The method of claim 1, wherein the first tissue anchor has a size different than a size of the second tissue anchor, and wherein implanting the first tissue anchor comprises implanting the first tissue anchor that has the size different to the size of the second tissue anchor.

10. The method of claim 1, wherein a proximal portion of the second tissue anchor is smaller than a distal portion thereof, and wherein implanting the second tissue anchor comprises implanting the second tissue anchor that has the proximal portion that is smaller than the distal portion.

11. The method of claim 1, further including the step of prior to pulling the first and second tissue anchors toward each other, injecting a space filling material into the LAA, wherein the space filling material is selected from a group consisting of: a solid, a liquid, a gas, a foam, and a gel.

12. The method of claim 11, wherein the space filling material comprises a first reagent and a second reagent, the second reagent being functional to activate the first reagent.

13. The method of claim 1, wherein the second tissue anchor is delivered by a tissue anchor delivery catheter and has a collapsed delivery profile and a radially expanded deployed configuration, wherein in the collapsed delivery profile, the second tissue anchor is elongated and is housed inside a lumen of the tissue anchor delivery catheter and in the radially expanded deployed configuration, the second tissue anchor expands radially and assumes at least one of an open umbrella shape and a plate shape.

14. The method of claim 13, wherein the second tissue anchor, in the radially expanded deployed configuration, comprises a continuous wire with spiral turns.

15. The method of claim 13, wherein the second tissue anchor, in the radially expanded deployed configuration, comprises multiple struts extending from a common center.

16. The method of claim 1, wherein inserting the locating wire across the atrial septum comprises piercing the atrial septum at the fossa ovalis using the locating wire.

17. The method of claim 1, wherein the first location is near an opening of the LAA, and wherein implanting the first tissue anchor comprises implanting the first tissue anchor such that (i) a distal portion of the first tissue anchor is placed against an outside of the LAA chamber, (ii) a proximal portion of the first tissue anchor is placed against an inside of the LAA chamber, and (iii) a tensioning member that extends along and passes through the first tissue anchor also extends proximally from the first tissue anchor and through a lumen of a tissue anchor delivery catheter to an outside of a patient's body.

* * * * *